(12) United States Patent
Taghizadeh

(10) Patent No.: US 9,198,735 B2
(45) Date of Patent: Dec. 1, 2015

(54) SYSTEM AND METHOD FOR PROVIDING TREATMENT FEEDBACK FOR A THERMAL TREATMENT DEVICE

(71) Applicant: Farhan Taghizadeh, Albuquerque, NM (US)

(72) Inventor: Farhan Taghizadeh, Albuquerque, NM (US)

( * ) Notice: Subject to any disclaimer, the term of this patent is extended or adjusted under 35 U.S.C. 154(b) by 0 days.

(21) Appl. No.: 14/510,047

(22) Filed: Oct. 8, 2014

(65) Prior Publication Data

US 2015/0025513 A1    Jan. 22, 2015

Related U.S. Application Data

(63) Continuation-in-part of application No. 14/245,973, filed on Apr. 4, 2014, and a continuation-in-part of application No. PCT/US2014/033026, filed on Apr. 4, 2014.

(60) Provisional application No. 61/809,544, filed on Apr. 8, 2013, provisional application No. 61/836,925, filed on Jun. 19, 2013.

(51) Int. Cl.
*A61B 18/02* (2006.01)
*A61B 19/00* (2006.01)
(Continued)

(52) U.S. Cl.
CPC .............. *A61B 19/5225* (2013.01); *A61B 18/02* (2013.01); *A61B 18/18* (2013.01);
(Continued)

(58) Field of Classification Search
CPC ........... A61B 2018/00458; A61B 2018/00464; A61B 2018/0047; A61N 5/025; A61N 2005/0642; A61N 2005/0643; A61F 2007/0087; A61F 2007/0088; A61F 2007/029
USPC .............. 606/27, 33, 34, 42; 607/96, 98–100, 607/102, 101, 115; 3/27, 33, 34, 42
See application file for complete search history.

(56) References Cited

U.S. PATENT DOCUMENTS 4,501,275 A * 2/1985 Maahs ............................ 607/81
5,553,618 A * 9/1996 Suzuki et al. .................. 600/411
(Continued)

FOREIGN PATENT DOCUMENTS

| JP | 2008-259631 A | 10/2008 |
|---|---|---|
| WO | WO 2011/132125 A1 | 10/2011 |
| WO | WO 2013/173516 A1 | 11/2013 |

OTHER PUBLICATIONS

Burdette, Clif E., et al. "Ultrasound Therapy Applicators for Controlled Thermal Modification of Tissue." Progress in Biomedical Optics and Imaging, 12(19) (2011).
(Continued)

*Primary Examiner* — Michael Peffley
*Assistant Examiner* — Thomas Giuliani
(74) *Attorney, Agent, or Firm* — Knobbe, Martens, Olson & Bear LLP

(57) ABSTRACT

A system and method for providing treatment feedback for a thermal treatment device (100) is provided. In certain embodiments, a thermal transmitter (120) is configured to apply an amount of thermal energy (104) to a target site (106), the thermal energy having a selected frequency and a selected power level for penetration to a depth beneath the surface of the skin. A thermal imager (140) is also provided, the thermal imager (140) being configured to capture thermal data and thermal images of the target site. The device may further provide a thermal display (160) configured to display the thermal images and thermal data, providing feedback to a user (201).

37 Claims, 31 Drawing Sheets

(51) Int. Cl.
  *A61F 7/00*    (2006.01)
  *A61B 18/18*   (2006.01)
  *A61N 5/02*    (2006.01)
  *A61N 5/06*    (2006.01)
  *A61F 7/10*    (2006.01)
  *A61F 7/02*    (2006.01)

(52) U.S. Cl.
  CPC ............ *A61B19/5212* (2013.01); *A61B 19/56* (2013.01); *A61F 7/00* (2013.01); *A61N 5/025* (2013.01); *A61N 5/0625* (2013.01); *A61F 7/10* (2013.01); *A61F 2007/0088* (2013.01); *A61F 2007/0095* (2013.01); *A61F 2007/029* (2013.01); *A61N 2005/0642* (2013.01); *A61N 2005/0644* (2013.01)

(56) References Cited

U.S. PATENT DOCUMENTS

| | | | |
|---|---|---|---|
| 6,023,637 | A | 2/2000 | Liu et al. |
| 6,413,255 | B1 * | 7/2002 | Stern .............................. 606/41 |
| 6,676,654 | B1 * | 1/2004 | Balle-Petersen et al. ......... 606/9 |
| 6,695,871 | B1 | 2/2004 | Naki et al. |
| 7,141,049 | B2 | 11/2006 | Stern et al. |
| 8,246,611 | B2 | 8/2012 | Paithankar et al. |
| 8,273,037 | B2 | 9/2012 | Kreindel et al. |
| 8,548,599 | B2 | 10/2013 | Zarsky et al. |
| 2003/0036751 | A1 * | 2/2003 | Anderson et al. ................. 606/9 |
| 2006/0009763 | A1 | 1/2006 | Goble et al. |
| 2006/0122508 | A1 | 6/2006 | Slayton et al. |
| 2006/0184163 | A1 | 8/2006 | Breen et al. |
| 2008/0058782 | A1 | 3/2008 | Frangineas et al. |
| 2008/0139974 | A1 | 6/2008 | Da Silva |
| 2008/0287930 | A1 | 11/2008 | Rapoport |
| 2010/0036378 | A1 | 2/2010 | Savery et al. |
| 2010/0249772 | A1 | 9/2010 | Mehta et al. |
| 2011/0015549 | A1 | 1/2011 | Eckhouse et al. |
| 2011/0245735 | A1 | 10/2011 | Eckhouse et al. |
| 2013/0197473 | A1 | 8/2013 | McMillan |
| 2013/0218021 | A1 | 8/2013 | Messano, Jr. et al. |
| 2013/0282083 | A1 | 10/2013 | Vertikov et al. |
| 2013/0289679 | A1 | 10/2013 | Eckhouse et al. |
| 2013/0331913 | A1 | 12/2013 | Levi et al. |

OTHER PUBLICATIONS

Elman, M., et al. Novel Multi-Source Phase-Controlled Radiofrequency Technology for Non-Ablative and Micro-Ablative Treatment of Wrinkles, Lax Skin and Acne Scars. Laser Therapy, 20(2), 139-144 (2011).

Skin Rejuvenation Clinic. "Dermesthetica". http://www.dermaesthetica.com/thermal-rejuvenation-facial-.html 2002. Page 1.

Johnson, Carolyn. Wand Used to Heat Wrinkles Away. http://abclocal.go.com/kgo/story?id=9110257 ABC 7 News. May 22, 2013.

Viora. Vtouch. http://www.vioramed.com/int/products/v-touch/ [Accessed Aug. 13, 2014]. pp. 5-6.

International Search Report and Written Opinion (PCT/ISA/220) issued Aug. 22, 2014 in PCT/US2014/033026, which corresponds to the present application.

International Search Report and Written Opinion (PCT/ISA/220) issued Feb. 13, 2015 in PCT/US2014/059782, which corresponds to the present application.

* cited by examiner

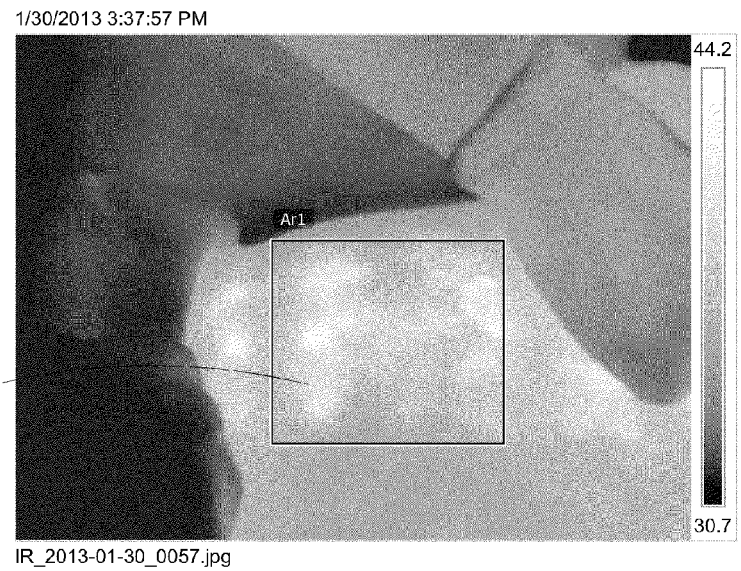
Fig.7A

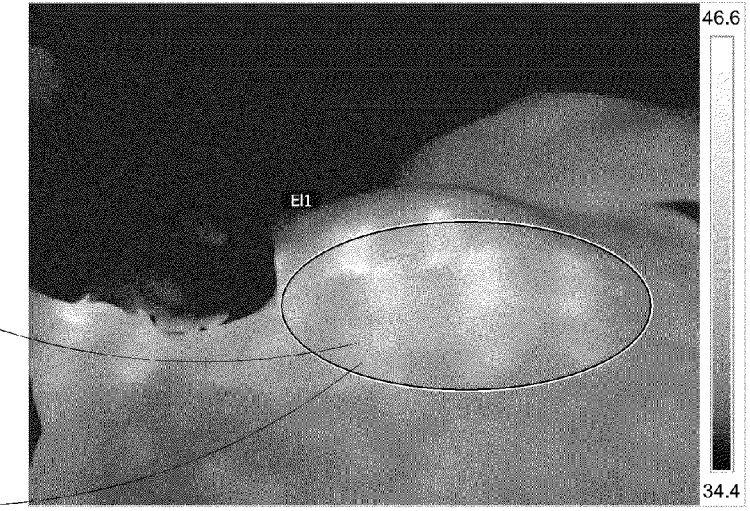
Fig. 7B

Fig.7C
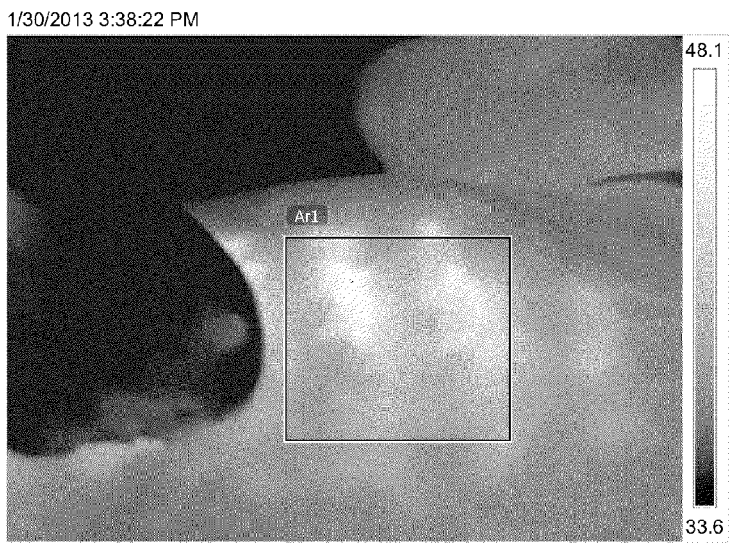
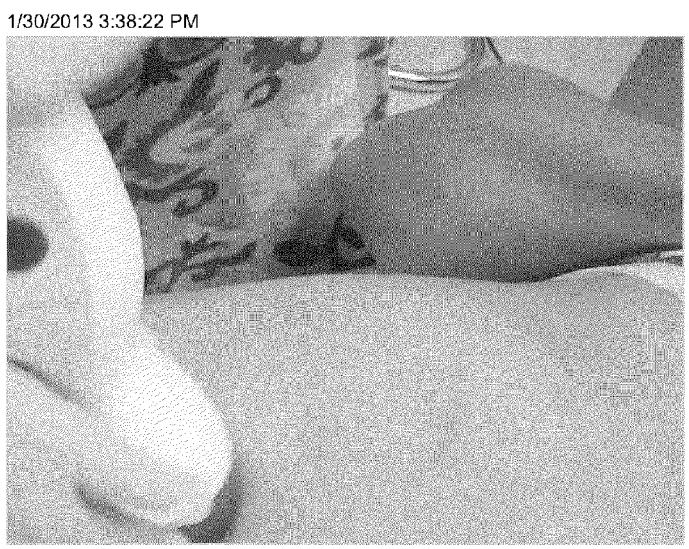

Fig.7D
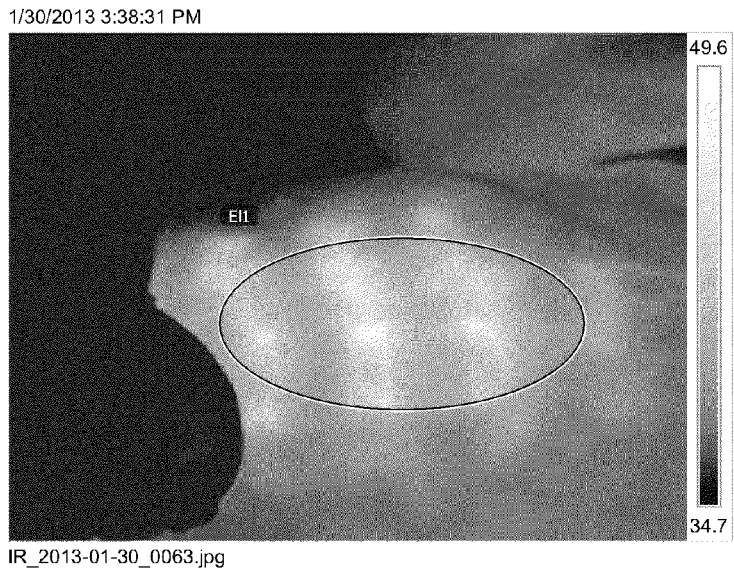

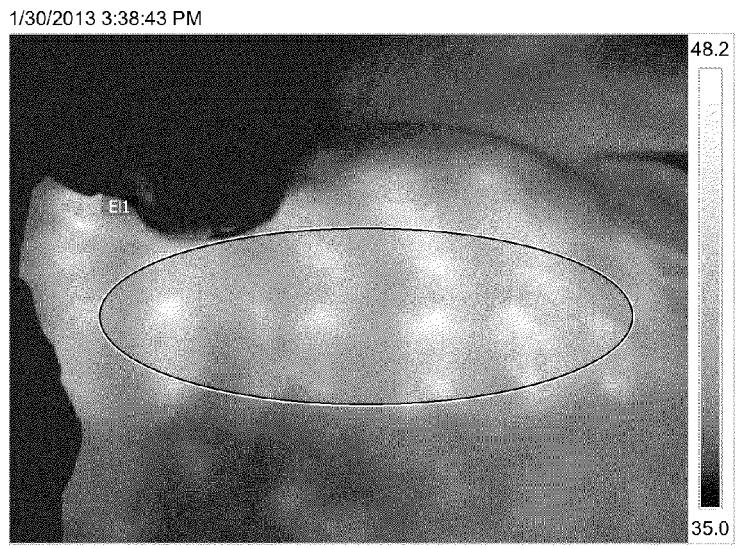
Fig.7E

Fig.7F
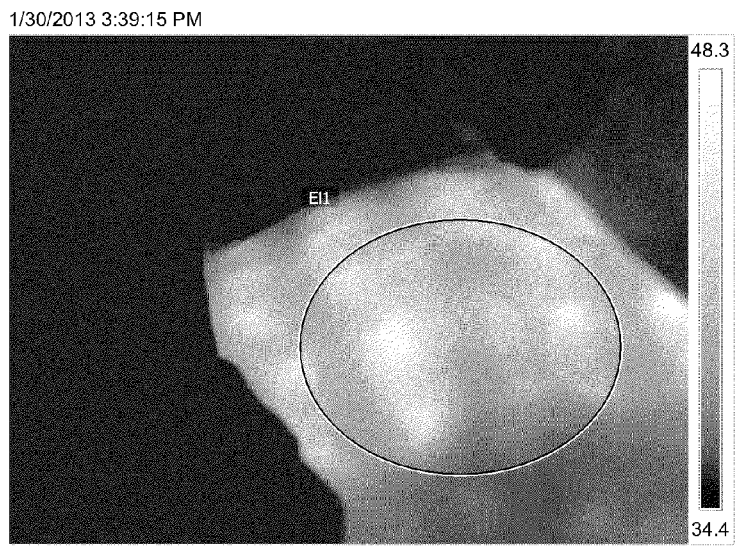

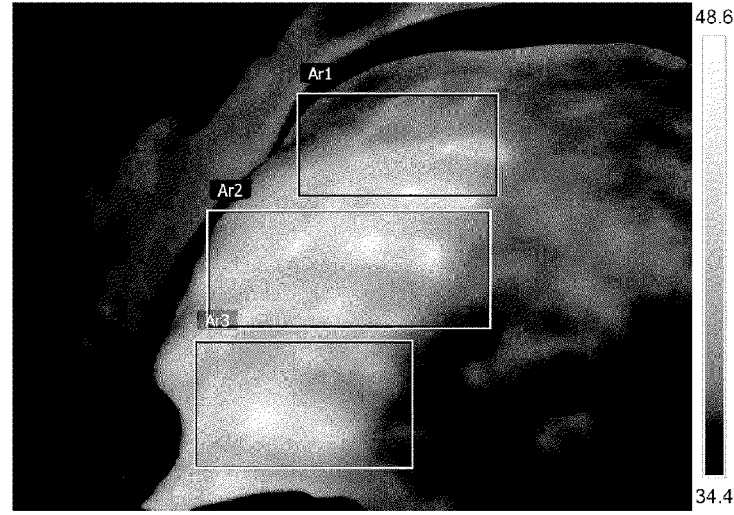
Fig. 7G

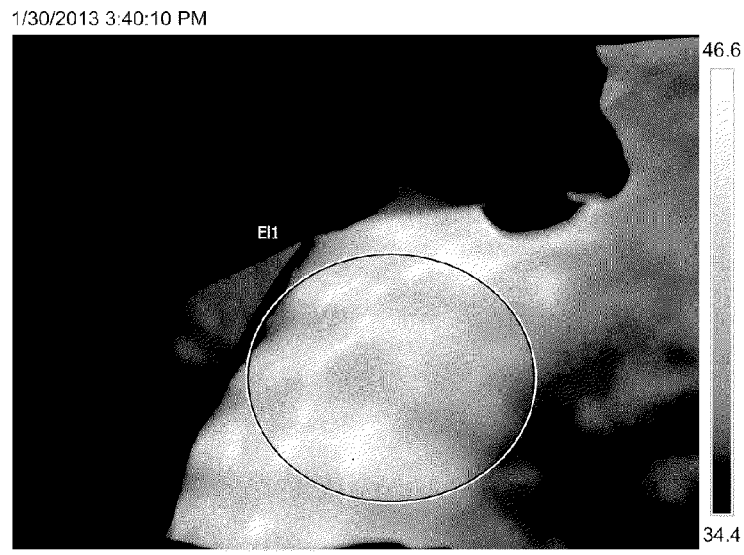
Fig. 7H

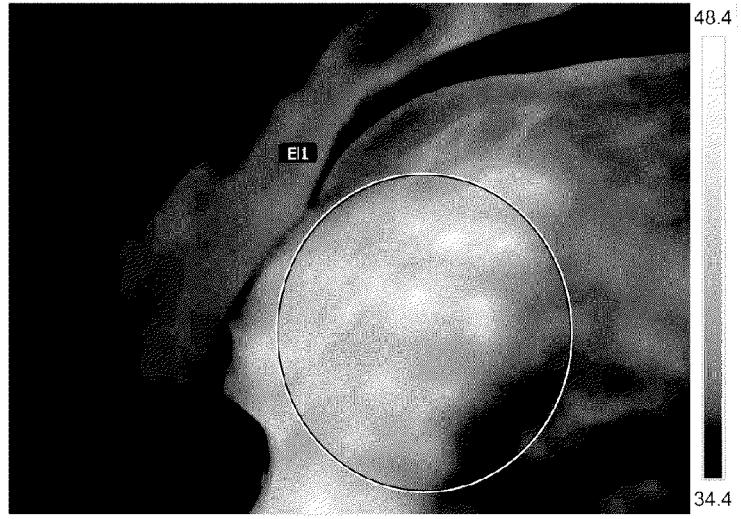
Fig. 7I

Fig. 7J
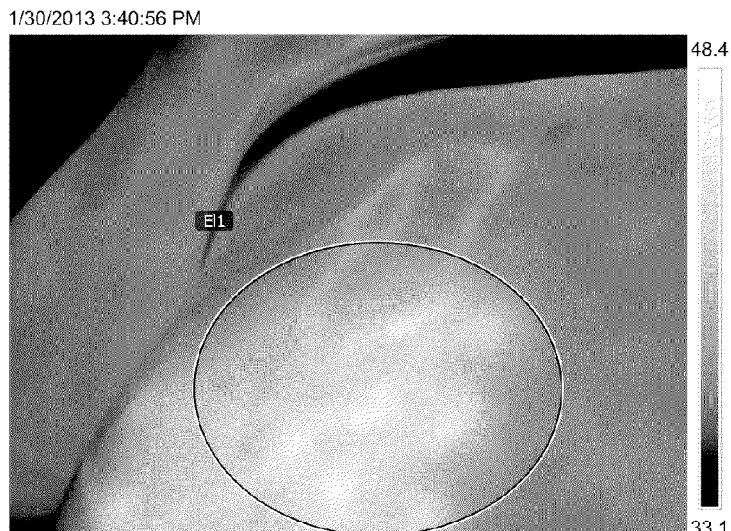

Fig.7K
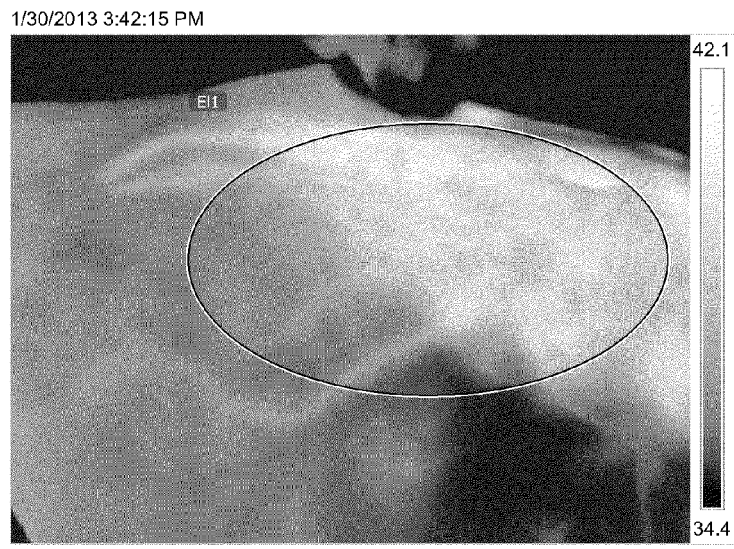

Fig. 7L
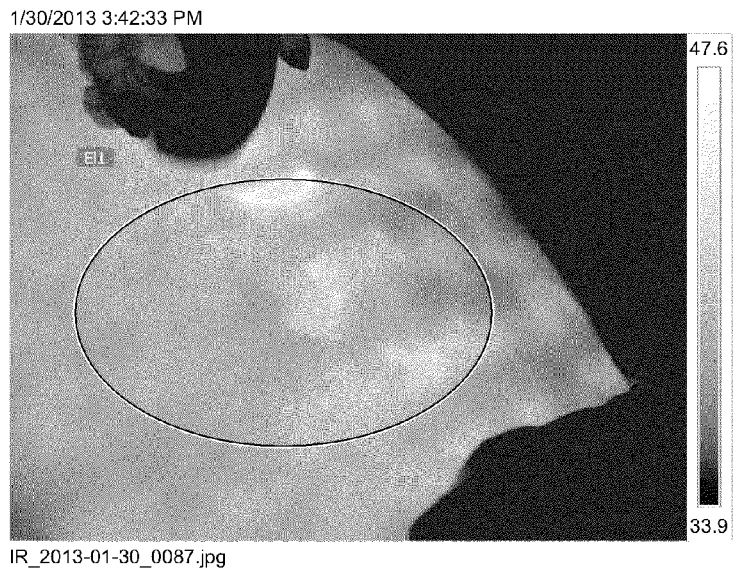

Fig.7M
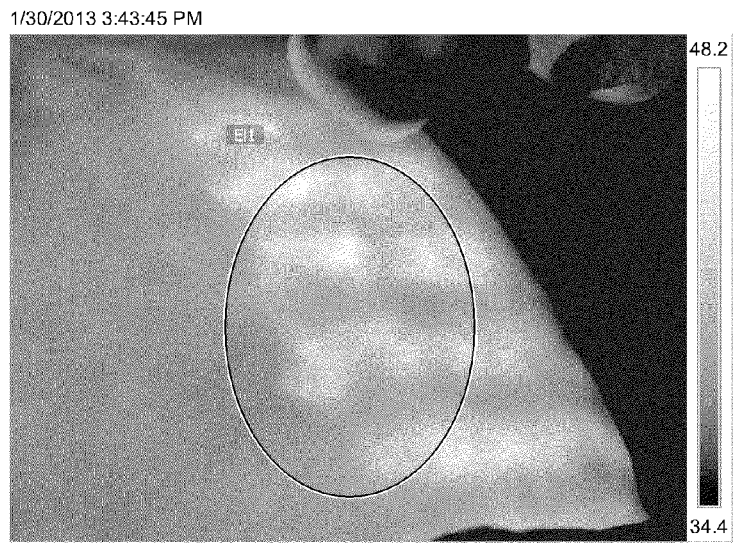

Fig.7N
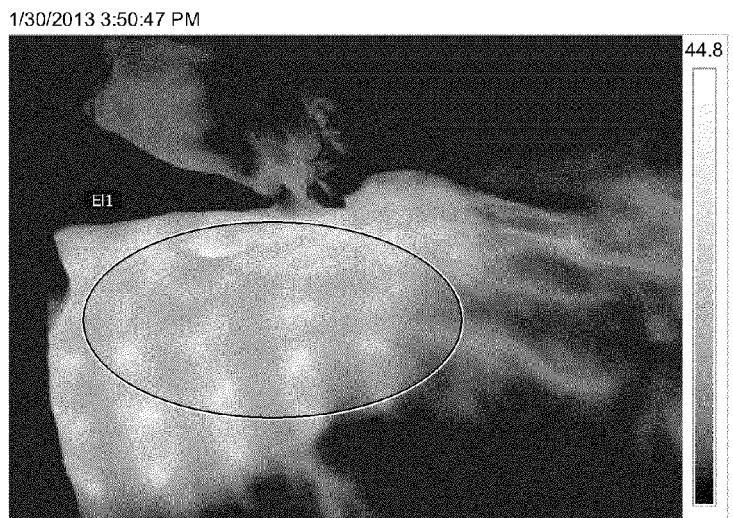

Fig. 70
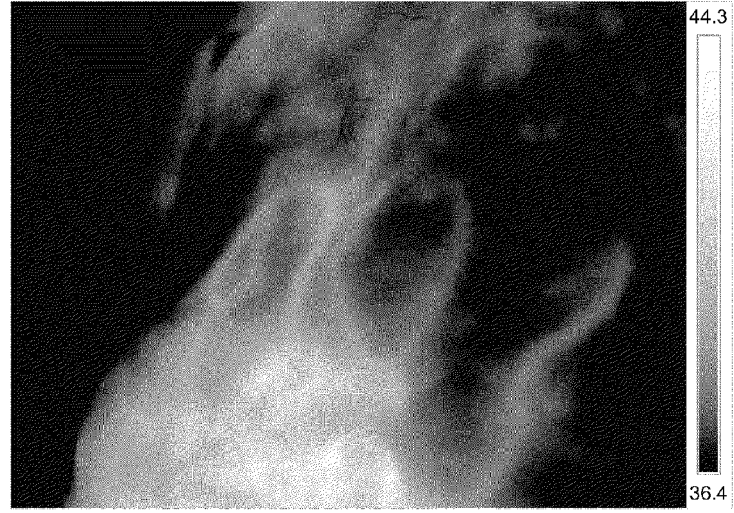

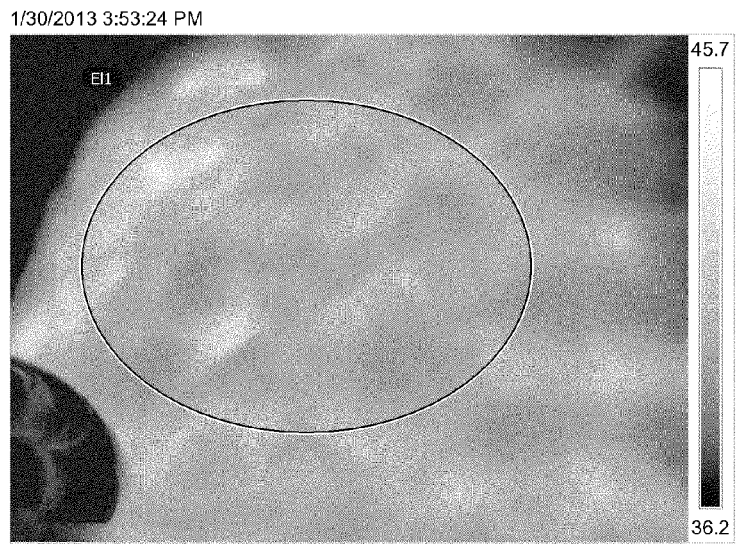
Fig.7P

fig. 7Q
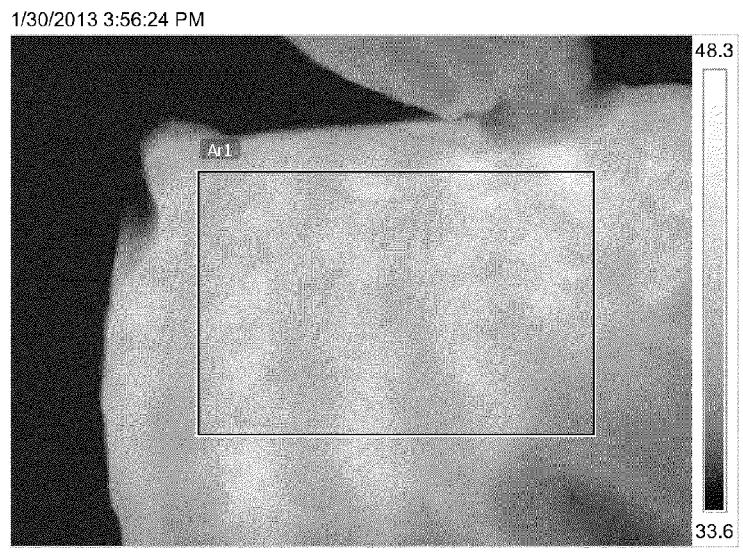

Fig. 7R
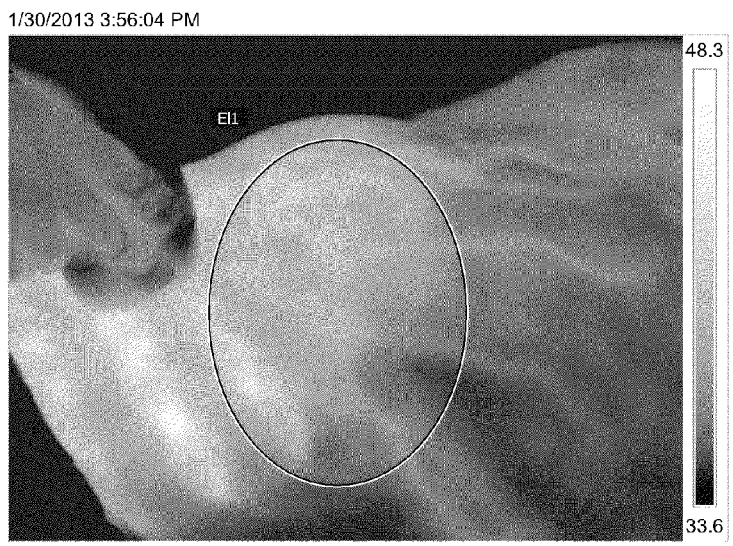

Fig.7S
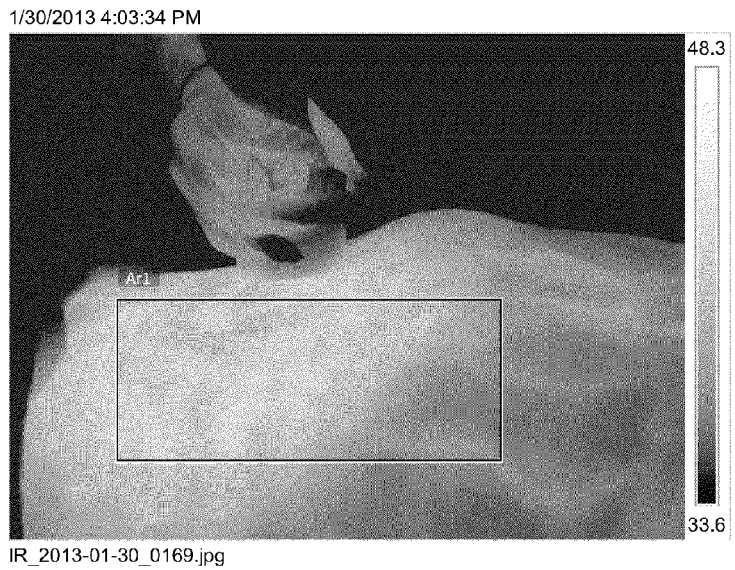

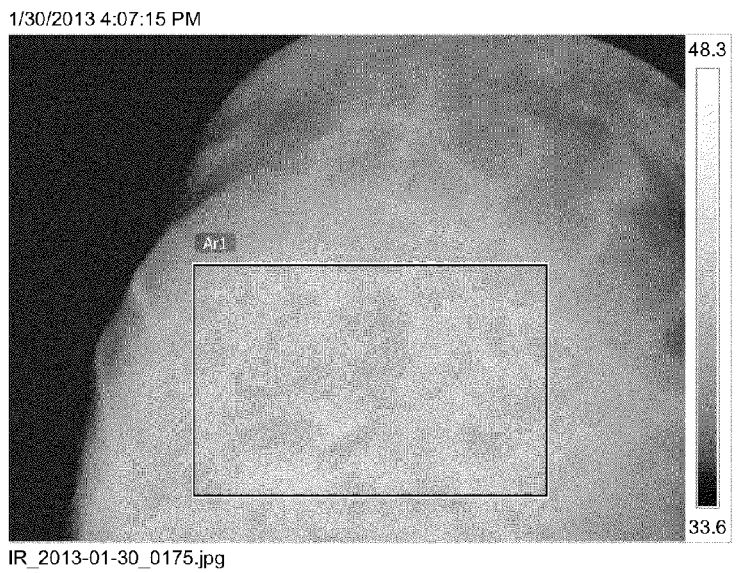
Fig.7T

SYSTEM AND METHOD FOR PROVIDING TREATMENT FEEDBACK FOR A THERMAL TREATMENT DEVICE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation-in-part of U.S. application Ser. No. 14/245,973, filed Apr. 4, 2014, and a continuation-in-part of PCT International Application No. PCT/US14/33026, filed Apr. 4, 2014. U.S. application Ser. No. 14/245,973 and PCT International Application No. PCT/US14/33026 each claim the benefit of U.S. Provisional Patent Application No. 61/809,544, filed Apr. 8, 2013, and U.S. Provisional Patent Application No. 61/836,925, filed Jun. 19, 2013. Each of the aforementioned applications is incorporated by reference herein in its entirety, and each is hereby expressly made a part of this specification.

BACKGROUND

1. Technological Field

This application relates generally to a thermal treatment device configured to administer heat for medical treatment. More particularly, this disclosure relates to a device for applying thermal energy to a target, monitoring the application of the via thermal energy imager on a display, and using the imagery to direct further application of energy.

2. Description of the Related Art

Thermal application devices may be used for heating the skin to initiate neocollagenesis, and skin tightening. Such devices may also be adapted to provide heat in the subcutaneous region so as to burn lipids. Such devices may be accomplished by targeting the desired area of treatment with heat in the form of a radio frequency ("RF") emitter. Use of a radio frequency allows heat energy to be applied at a desired depth below the surface of the skin (epidermis).

Therefore it would be advantageous to provide a system configured to apply thermal energy to a treatment area that provides timely feedback data regarding the treated area for subsequent application of energy.

SUMMARY

In a first aspect (for example independently combinable with any of the aspects or embodiments identified herein), a thermal treatment system is provided, comprising: a thermal transmitter configured to apply an amount of thermal energy to a target site, the thermal energy having a selected frequency or wavelength, a selected power level, and a direction. The system may further comprise a thermal imager configured to capture thermal data and thermal images of the target site. The system may further comprise a thermal display configured to display the thermal data and the thermal images.

In an embodiment of the first aspect, which is generally applicable (for example, independently combinable with any of the aspects or embodiments identified herein), the system may further comprise a user interface allowing a selection of a routine for the application of thermal treatment to the target site, the routine comprising instructions for the application of the thermal energy, at least one processor configured to process the thermal images and thermal data according to the selected routine, and a controller configured to indicate on the display a required adjustment to the selected frequency or wavelength and the selected power level of the thermal transmitter, or command an adjustment to the selected frequency or wavelength and the selected power level of the thermal transmitter, based on the thermal data and the thermal images, according to the selected routine.

In an embodiment of the first aspect, which is generally applicable (for example, independently combinable with any of the aspects or embodiments identified herein), the system may further comprise a radio frequency transmitter configured to transmit the thermal energy to the target site at a depth below the surface of the skin and a mechanical drive configured to receive commands from a controller to adjust the direction of the applied thermal energy.

In an embodiment of the first aspect, which is generally applicable (for example, independently combinable with any of the aspects or embodiments identified herein), the system may further comprise an infrared transmitter configured to transmit the thermal energy to the target site at a depth below the surface of the skin and a mechanical drive configured to receive commands from a controller to adjust the direction of the applied thermal energy.

In an embodiment of the first aspect, which is generally applicable (for example, independently combinable with any of the aspects or embodiments identified herein), the system may further comprise a memory configured to store information related to the execution of the selected routine, the memory being accessible by the processor, the thermal transmitter, and the thermal imager, and the memory further comprising at least one database for storing a plurality of routines.

In an embodiment of the first aspect, which is generally applicable (for example, independently combinable with any of the aspects or embodiments identified herein), the system may further comprise a wireless communication link operationally connecting the thermal transmitter, the thermal imager, and the thermal display.

In an embodiment of the first aspect, which is generally applicable (for example, independently combinable with any of the aspects or embodiments identified herein), the display may be configured to display the thermal images and a gradient map, the gradient map being configured to depict a plurality of temperatures of the tissue at the target site, at a selected depth below the surface of the skin.

In an embodiment of the first aspect, which is generally applicable (for example, independently combinable with any of the aspects or embodiments identified herein), the thermal imager may be configured to provide thermal data at a position in the tissue anywhere in the range from the surface of the skin to 15,000 micrometers below the surface of the skin.

In an embodiment of the first aspect, which is generally applicable (for example, independently combinable with any of the aspects or embodiments identified herein), the system may further comprise the thermal transmitter may be further configured to transmit thermal energy to a selected depth anywhere in the range of zero to 15,000 micrometers below the surface of the skin at the target site.

In an embodiment of the first aspect, which is generally applicable (for example, independently combinable with any of the aspects or embodiments identified herein), the thermal transmitter may be further configured to heat the tissue beneath the target site to a temperature anywhere in the range from 35 degrees Celsius to 50 degrees Celsius.

In an embodiment of the first aspect, which is generally applicable (for example, independently combinable with any of the aspects or embodiments identified herein), the thermal transmitter, the thermal imager, and the thermal display may be configured in a unitary handheld unit.

In an embodiment of the first aspect, which is generally applicable (for example, independently combinable with any of the aspects or embodiments identified herein), the unitary handheld unit may comprise a link powering the unitary handheld unit; the link may be further configured to provide communication with at least one external processor.

In an embodiment of the first aspect, which is generally applicable (for example, independently combinable with any of the aspects or embodiments identified herein), the thermal transmitter may be further configured to cryogenically cool the tissue at the target site to a temperature range anywhere from 10 degrees Celsius to negative 20 degrees Celsius.

In an embodiment of the first aspect, which is generally applicable (for example, independently combinable with any of the aspects or embodiments identified herein), the thermal display may be configured to display at least one of: the thermal images, the thermal data, and the gradient map, the gradient map indicating graphical depiction of the temperatures of the tissue at the target site at the selected depth.

In a generally applicable second aspect (for example independently combinable with any of the aspects or embodiments identified herein), a method is provided for applying thermal treatment, comprising, providing a target site on a patient, the target site comprising tissue having certain characteristics, positioning a thermal transmitter, the thermal transmitter configured to transmit thermal energy toward the target site, applying the thermal energy to the target site according to a thermal treatment routine, the thermal energy having a selected frequency or wavelength, a selected power level, and a direction, capturing thermal data and thermal images of the target site with a thermal imager, the thermal data and thermal images corresponding to a tissue temperature at the target site, and displaying the thermal data and the thermal image of the target site on a thermal display.

In an embodiment of the second aspect, which is generally applicable (for example, independently combinable with any of the aspects or embodiments identified herein) the method may, further comprise, selecting the thermal treatment routine according to the characteristics, monitoring the thermal images and the thermal data for an optimum tissue temperature, and adjusting the selected frequency or wavelength, the selected power level, or the direction, according to the monitoring and the selected routine.

In an embodiment of the second aspect, which is generally applicable (for example, independently combinable with any of the aspects or embodiments identified herein) the method may, further comprise, applying the thermal energy to the tissue at the target site at a depth beneath the surface of the skin.

In an embodiment of the second aspect, which is generally applicable (for example, independently combinable with any of the aspects or embodiments identified herein) the method may further comprise storing information related to the execution of the selected routine in a memory accessible by the processor, the thermal transmitter, and the thermal imager, the memory further comprising at least one database for storing a plurality of routines.

In an embodiment of the second aspect, which is generally applicable (for example, independently combinable with any of the aspects or embodiments identified herein) the method may further comprise, wirelessly communicating the thermal data and the thermal images from the thermal imager to the thermal display; and wirelessly communicating a plurality of control signals from a controller to the thermal transmitter and the thermal imager.

In an embodiment of the second aspect, which is generally applicable (for example, independently combinable with any of the aspects or embodiments identified herein) the method may further comprise, displaying the thermal data and the thermal images on a gradient map, the gradient map configured to depict a plurality of temperatures of the tissue at the target site the a selected depth beneath the surface of the skin.

In an embodiment of the second aspect, which is generally applicable (for example, independently combinable with any of the aspects or embodiments identified herein) the thermal imager may be configured to provide thermal data at a position within the tissue anywhere in a range from a surface of the skin to 15,000 micrometers below the surface of the skin.

In an embodiment of the second aspect, which is generally applicable (for example, independently combinable with any of the aspects or embodiments identified herein) the thermal transmitter may be configured to transmit thermal energy to a selected depth anywhere in a range from a surface of the skin to 15,000 micrometers below the surface of the skin at the target site.

In an embodiment of the second aspect, which is generally applicable (for example, independently combinable with any of the aspects or embodiments identified herein) the thermal transmitter may be further configured to heat the tissue at the target site to a temperature anywhere in a range of from 35 degrees Celsius to 50 degrees Celsius.

In an embodiment of the second aspect, which is generally applicable (for example, independently combinable with any of the aspects or embodiments identified herein) the thermal transmitter may be further configured to cryogenically cool the tissue at the target site to a temperature anywhere in a range of from 10 degrees Celsius to negative 20 degrees Celsius.

In an embodiment of the second aspect, which is generally applicable (for example, independently combinable with any of the aspects or embodiments identified herein) the thermal display may be configured to display at least one of the thermal images, the thermal data, and the gradient map, the gradient map indicating graphical depiction of the temperatures of the tissue at the target site at the selected depth In a generally applicable third aspect (for example independently combinable with any of the aspects or embodiments identified herein), an apparatus is provided for thermal treatment comprising, means for selecting a thermal heating routine, means for heating a target site, means for sensing thermal emittance of the target site, means for providing feedback to a user, and means for adjusting the application of the thermal energy according to the feedback and the thermal heating routine.

In a generally applicable fourth aspect (for example independently combinable with any of the aspects or embodiments identified herein), a non-transitory, computer readable medium is provided, that when executed by a processor is configured to, position a thermal transmitter, the thermal transmitter configured to transmit thermal energy toward a selected target site on a patient, apply the thermal energy to the target site according to a thermal treatment routine, the thermal energy having a selected frequency, a selected power level, and a direction, capture thermal data and thermal images of the target site with a thermal imager, the thermal data and thermal images corresponding to a skin temperature at the target site, display the thermal data and the thermal image of the target site on a thermal display, and adjust at least one of the selected frequency, the selected power level, and the direction, according the thermal treatment routine.

In a generally applicable fifth aspect (for example independently combinable with any of the aspects or embodiments identified herein), a method for applying thermal treatment, comprising is provided according to the figures and steps disclosed herein.

In a generally applicable sixth aspect (for example independently combinable with any of the aspects or embodiments identified herein), an apparatus method for applying thermal treatment, comprising is provided, according to the figures and characteristics disclosed herein.

Any of the features of an embodiment of the first through sixth aspects is applicable to all aspects and embodiments identified herein. Moreover, any of the features of an embodiment of the first through sixth aspects is independently combinable, partly or wholly with other embodiments described herein in any way, for example, one, two, or three or more embodiments may be combinable in whole or in part. Further, any of the features of an embodiment of the first through third aspects may be made optional to other aspects or embodiments. Any aspect or embodiment of a method can be performed by a system or apparatus of another aspect or embodiment, and any aspect or embodiment of a system can be configured to perform a method of another aspect or embodiment.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

FIG. 7A depicts readings of a thermal imager that implemented to provide feedback, according to some embodiments of the present disclosure;

FIG. 7B depicts readings of a thermal imager that implemented to provide feedback, according to some embodiments of the present disclosure;

FIG. 7C depicts readings of a thermal imager that implemented to provide feedback, according to some embodiments of the present disclosure;

FIG. 7D depicts readings of a thermal imager that implemented to provide feedback, according to some embodiments of the present disclosure;

FIG. 7E depicts readings of a thermal imager that implemented to provide feedback, according to some embodiments of the present disclosure;

FIG. 7F depicts readings of a thermal imager that implemented to provide feedback, according to some embodiments of the present disclosure;

FIG. 7G depicts readings of a thermal imager that implemented to provide feedback, according to some embodiments of the present disclosure;

FIG. 7H depicts readings of a thermal imager that implemented to provide feedback, according to some embodiments of the present disclosure;

FIG. 7I depicts readings of a thermal imager that implemented to provide feedback, according to some embodiments of the present disclosure;

FIG. 7J depicts readings of a thermal imager that implemented to provide feedback, according to some embodiments of the present disclosure;

FIG. 7K depicts readings of a thermal imager that implemented to provide feedback, according to some embodiments of the present disclosure;

FIG. 7L depicts readings of a thermal imager that implemented to provide feedback, according to some embodiments of the present disclosure;

FIG. 7M depicts readings of a thermal imager that implemented to provide feedback, according to some embodiments of the present disclosure;

FIG. 7N depicts readings of a thermal imager that implemented to provide feedback, according to some embodiments of the present disclosure;

FIG. 7O depicts readings of a thermal imager that implemented to provide feedback, according to some embodiments of the present disclosure;

FIG. 7P depicts readings of a thermal imager that implemented to provide feedback, according to some embodiments of the present disclosure;

FIG. 7Q depicts readings of a thermal imager that implemented to provide feedback, according to some embodiments of the present disclosure;

FIG. 7R depicts readings of a thermal imager that implemented to provide feedback, according to some embodiments of the present disclosure;

FIG. 7S depicts readings of a thermal imager that implemented to provide feedback, according to some embodiments of the present disclosure;

FIG. 7T depicts readings of a thermal imager that implemented to provide feedback, according to some embodiments of the present disclosure; and.

DETAILED DESCRIPTION

Figure 1:
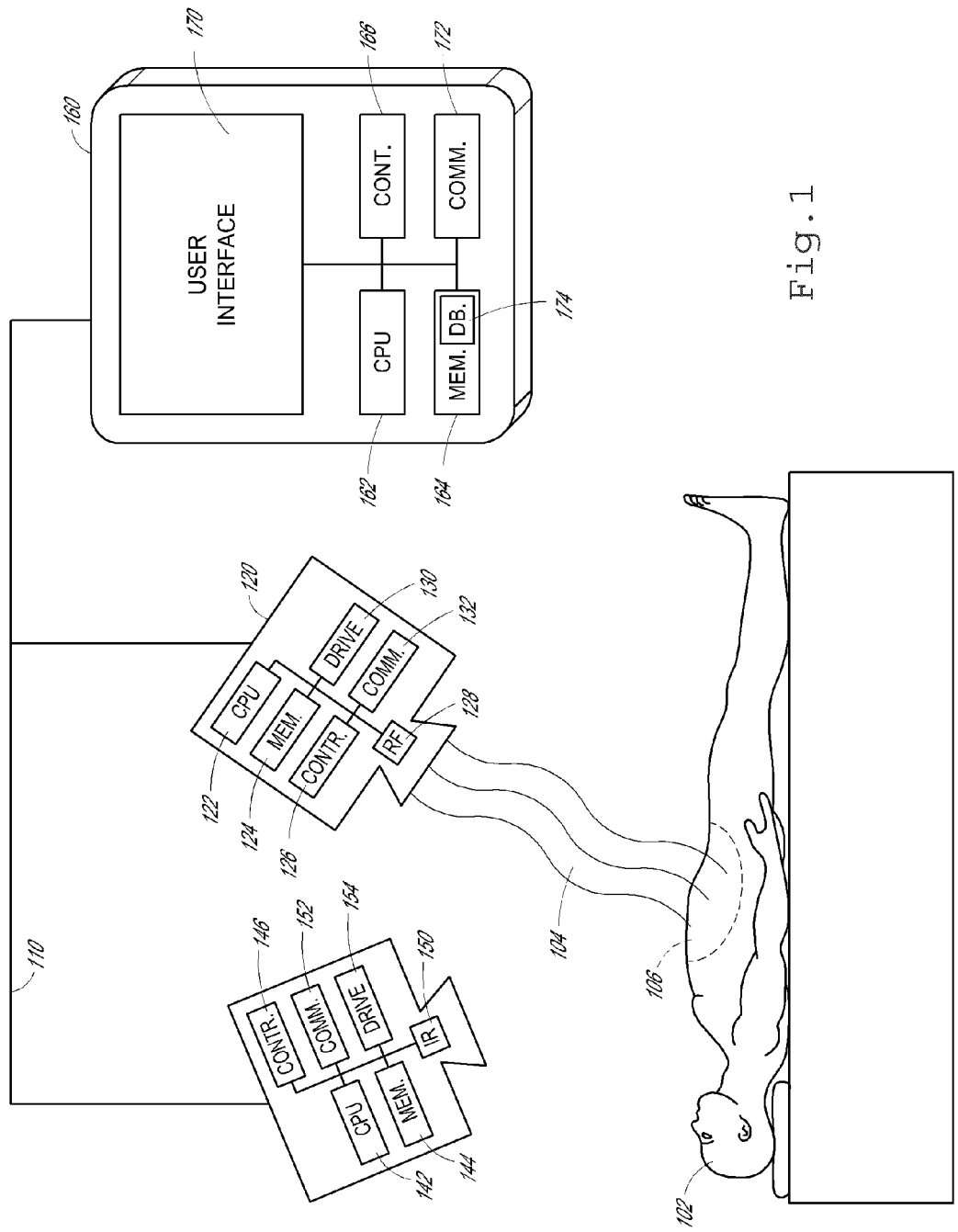
FIG. 1 is a functional block diagram of a system for application of therapeutic thermal energy according to the disclosure.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure.

The application of thermal energy to a patient's skin for medical or therapeutic reasons can have positive effects. Certain thermal energy application systems may be able harnesses these beneficial properties through the use of RF energy, microwave energy, direct heating (convective, conductive) systems, ultrasound, light (for example, proton) energy, and certain lasers system, among others. For purposes of this disclosure, RF will refer to the frequencies falling between 3 hertz (Hz) and 300 gigahertz (GHz), while overlapping with microwave radiation in the range of 300 megahertz (Mhz) to 300 GHz.

Medical uses of RF are based on an oscillating electrical current forcing collisions between charged molecules and ions that are transformed into heat experienced at the target space. RF heating occurs irrespective of chromophore (color of the molecule) or skin type and is not dependent on selective photothermolysis. RF energy can be delivered using monopolar, bipolar, and unipolar devices, and each RF delivery method has theoretical limits regarding the depth of skin penetration.

RF thermal stimulation is believed to result in a microinflammatory process that promotes new collagen, tightening the skin at a target site. By manipulating skin cooling, RF can also be used for heating and reduction of fat. RF-based devices may further be configured to noninvasively achieve skin tightening and body contouring.

RF energy may be imparted to and/or incident on the skin, manifesting as heat within the targeted areas including depths within the skin. Application depth and area may be dependent upon the intensity of the energy source, and the frequency and wavelength of the energy waves. These systems may be employed in medical or therapeutic environments to provide aesthetic results by melting subcutaneous (for example, below the skin) fat and tightening skin, for a more youthful appearance.

Certain thermal treatment systems may further incorporate infrared (IR) energy emissions in the near-, mid-, or far-IR bands. Infrared light (also referred to herein as IR energy) is electromagnetic radiation with longer wavelengths than those of visible light, extending from the nominal red edge of the visible spectrum at 700 nanometers (nm) to 1 mm. This range of wavelengths corresponds to a frequency range of approximately 430 terahertz (THz) down to 300 GHz. IR energy may be applied to a target through the use of heating elements (metallic or ceramic heating elements) or IR light emitting diode (LED) directed at the target. IR energy may be used both as a heat source, but also as a way to monitor the amount of thermal energy applied to a target, as discussed below. Most of the heat, or thermal radiation, emitted by objects, is also detectable as infrared energy. This detectable energy may be captured and represented as thermal imagery.

Some thermal therapy systems may emit a constant, or steady flow of energy, while others implement a system using periodic bursts of energy to heat the skin and/or areas below the surface of the skin to achieve the desired effects. Other disclosed systems may utilize a hybrid having a mix of the peaks or bursts of energy and steady energy emissions, having a custom or user-programmable profile emitting energy at different times and different areas of the body. For example, a treatment procedure on the face will encounter generally thinner skin than a procedure on the abdomen; accordingly, penetration depth of the RF energy should generally be shallower on the face than the abdomen.

Certain thermal treatment systems or devices provide a self-contained apparatus that an individual may implement. Alternatively, a clinician may apply the thermal energy for a specific medical process or procedure. Some systems may control thermal energy flow through a measurement of total energy emitted from the device or through the use of feedback controls such as a temperature sensor adjacent to or in contact with the skin, or on the output of the thermal application device, or through the use of thermal imaging.

Certain embodiments may have an indicator projected onto the skin, indicating an area of the skin where energy is applied. In an embodiment, a laser pointer or a light emitting diode (LED) may be implemented within the device providing a sight or indicator to the user for directing the application of the energy. Certain embodiments may further comprise a measurement of how much energy is being emitted by the system and directed toward the skin.

Certain embodiments may further have a thermal imaging system providing a qualitative or quantitative indication of how much energy is being absorbed by the skin. As the energy (for example, RF, heat, light (including for example, laser, LED), microwave, ultrasonic) is directed toward the skin, the frequency and wavelength of the energy may affect the amount of energy actually absorbed and at what depth beneath the surface of the skin. A thermal camera implemented as a feedback system may provide a color gradient indicating the area of the skin heated by the system. Such qualitative feedback may be used to show the parts of the skin that have been heated as indicated by the colored gradient (for example, red for higher heat, yellow or orange for medium heat) ensuring the user can apply the energy and heat the skin in a desired manner. Certain other embodiments may correlate the colored gradient to specific temperatures or temperature ranges, giving a quantitative output to the user or precise feedback to the system, allowing a more precise application of energy to the skin.

Certain embodiments may further provide an indication of specific temperatures at different levels beneath the skin. While the thermal transmitter may be calibrated in frequency and wavelength to target energy to a specific layer of skin or adipose tissue (superficial skin to 15,000 μm or more beneath the surface, e.g., down to 14,000, 13,000, 12,000, 11,000, 10,000, 9,000, 8,000, 7,000, 6,000, 5,000, 4,000, 3,000, 2,000, 1,000, 750, 500, or 250 μm), the thermal imager may further be configured to detect local temperatures at a specific level beneath the skin, providing the system and the user with specific feedback as to where the energy should be directed. This information may be provided to the thermal display.

In certain embodiments, a processor may be implemented in the system that may process the feedback provided by the thermal camera for directing the user's application of energy. The directions provided by the processor may be in accordance with a specific program or therapeutic process. A thermal display may be used to direct the application of energy, while also providing feedback regarding the energy already applied. The processor may direct the user where to apply the energy according to the program selected.

In certain embodiments, the system may further comprise additional processor(s) automatically analyzing the thermal image feedback. Such an embodiment may comprise a thermal transmitter, a thermal imager, and one or more processors that autonomously direct the application of the energy without user input.

FIG. 1 depicts a system 100 for administering thermal treatment according to the disclosure. As shown, a patient 102 is receiving therapeutic RF energy 104 at a target site 106. The system 100 administers and controls the emission and measurement of the RF energy 104. While referred to herein as "RF energy," the energy 104 may also be implemented in the IR or microwave ranges. In certain embodiments, the IR and/or microwave transmissions may complement the RF transmissions, optimizing the energy absorption by the skin at the target site 102.

In an embodiment, the system 100 comprises a thermal transmitter 120, a thermal imager 140, and a thermal display 160. The thermal transmitter 120, the thermal imager 140, and the thermal display 160 are shown located remotely from each other, however as shown below, the various components of system 100 may be collocated in a fewer components, comprising two or more of the listed elements (for example, the thermal transmitter 120, the thermal imager 140, and the thermal display 160), or in a unitary embodiment as shown below. Each of the components, the thermal transmitter 120, the thermal imager 140, and the thermal display 160 are depicted as functional block diagrams with each block representing a portion of the internal electronics of each component as described.

The thermal transmitter 120 may be a handheld device, as shown below in FIG. 2 and FIG. 3, or be constructed on an autonomous or computer-driven, motorized mount. In some embodiments, the thermal transmitter 120 comprises a processor 122 (also referred to herein as a "CPU") operationally coupled to a memory ("mem.") 124 configured to store executable programs, operating systems, or certain data required for operation of the thermal transmitter 120. The thermal transmitter 120 may further comprise a controller ("contr.") 126 operationally coupled to the processor 122 and the memory 124 and configured to control the operations of the thermal transmitter 120. The thermal transmitter 120 may further comprise an RF transmitter 128 coupled to at least the processor 122 and the controller 106. The RF transmitter 128 may be configured to transmit RF energy 104 directed to a target site 106 on the skin of a patient 102 as disclosed herein. In another embodiment, the RF transmitter 128 may be alternatively configured as an IR transmitter. In another embodiment, both the thermal transmitter 120 may be configured with the RF transmitter 128 and an IR transmitter.

In an embodiment, the thermal transmitter 126 may further comprise a mechanical drive 130, operationally coupled to the controller 126. The mechanical drive 130 may be employed to autonomously move the thermal transmitter 120 using feedback from one or more CPU 122 or user input via a user interface, described below. In an embodiment, the mechanical drive 130 may be optional if the system 100 is employed as a handheld device, as discussed with respect to FIG. 2.

The processor 122 may be further configured to receive input from other components (for example, the thermal imager 140 and the thermal display 160), analyze the input, and provide commands to the controller 126 to adjust the frequency, wavelength, and/or power level of the emitted RF energy 104 from RF transmitter 128. In an embodiment, the thermal imager 140 may receive thermal information, comprising thermal images of the target site 106 discussed below, as feedback and control information that the thermal transmitter 120 may use to adjust RF emissions 104.

The thermal transmitter 120 may further comprise a communications controller ("comm.") 132 operationally coupled to the processor 122 configured to transmit and receive information and commands from the thermal imager 140 and/or the thermal display 160 via a communication link 110. The communications controller 132 may communicate with the analogous communications controllers (discussed below) on the thermal imager 140 and the thermal display 160. The processor 122 may receive thermal or other sensory information from the thermal imager 120 via the communication link 110 and be further configured to process the sensory information and adjust the emitted RF energy 104, as required by a selected routine (discussed below) or by direct user input.

A communication link 110 may be implemented as a wireless connection or as a wired connection between the various components of system 100. In an embodiment, the communication link 110 may comprise a wireless (for example, Wi-Fi) network. The communication links 110 implemented as a wireless connection may comprise a Wi-Fi™ or Bluetooth™ transceiver or other suitable wireless communication protocols.

The thermal transmitter 120, and more specifically, the RF transmitter 128, may be configured to administer thermal energy in the RF spectrum directed at a target site 106 on the skin of a patient 102. The thermal energy may be adjusted to penetrate to a desired depth within the skin of the patient 102. Such RF energy 104 may be referred to as "thermal energy" herein based on the localized heating that results from the impact of the charged RF particles on the target molecules within the skin, as noted above.

The type of energy type, frequency, and wavelength of the emissions from RF transmitter 128 may be varied according to the type or intensity of therapy desired. In an embodiment, the thermal transmitter 120 may operate in an RF/microwave range at approximately 3 Hz nm-300 GHz, outside of the visible light spectrum, but above that of IR (1 mm-$10^4$ Km). Certain other embodiments the thermal transmitter may further comprise laser or ultrasound transmitters (in addition to or in place of the RF transmitter 128) for the introduction of heat energy below the surface of the skin. The frequency and wavelength of the imparted energy may be optimized such that it is absorbed at specific depths of skin without extreme superficial heating that may cause discomfort or burns.

In an embodiment, the thermal transmitter 120 is configured to administer heat the target site 106 to a temperature in the range of 38° Celsius and 42° Celsius. In some embodiments, the thermal transmitter 120 is configured to administer heat the target site 106 to a temperature of about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, or 95° Celsius or higher, preferably from about 35 to about 50° Celsius, or from about 40 to about 50° Celsius, or from about 45 to about 50° Celsius, or any number or range therebetween. In some embodiments, the skin may be heated for about 0.1 minute or less, or 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or more or any number or ranger therebetween, e.g., from about 0.1 minute to 15 minutes, or from about 1 minute to about 10 minutes. In certain embodiments, the skin may be heated to 47° Celsius for certain applications for as long as ten minutes to achieve optimum results. In certain embodiments, heating energy should be applied to skin to heat the skin to 37° Celsius for seven minutes for optimum results for certain lipolysis treatments. The amount of heat administered may be adjusted by reducing or increasing the rate at which the heat is emitted, or increasing the energy of the transmission.

In an embodiment, the use of the RF energy 104 may allow the clinician to heat the target site 106 from a distance (remotely, for example) without actually contacting the skin. However, while FIG. 1 depicts a thermal transmitter 120 not in contact with the target site 106, certain embodiments may contact the skin at the target site 106 as required. In another embodiment, at least a portion the thermal transmitter may contact the skin at the target site 106, as shown in FIG. 7A-FIG. 7T. In an embodiment providing contact between the thermal transmitter 120 and the target site 106, certain sensors (not shown) may be collocated with the thermal transmitter 120. Such sensors may further comprise a thermistor or thermometer to sense local skin temperature (degrees). The thermal transmitter 120 may further comprise a plurality of electrodes configured to sense skin impedance (ohms) and in order to further regulate the application of energy 104.

The thermal treatment selected for use with the systems and devices disclosed herein may further consider lipolysis that occurs at colder temperatures as well. Cryolipolysis may occur from temperatures ranging from +10° C. down to −20° C. where frostbite occurs. In an embodiment, the colder temperatures targeted by the thermal treatment system 100 may be from +10° C. to −15° C., as needed, or from +10° C. to −10° C., or from +10° C. to −5° C., or from +10° C. to 0° C., or from 0° C. to −15° C., or from 0° C. to −10° C., or from 0° C. to −5° C. In such an embodiment, the thermal transmitter 120 may be fitted with cooling elements (not shown) that may contact the skin at the target site 106. The cooling elements may be serve to prevent patient 102 discomfort or superficial burns at the target site 106 during energy 104 application.

In certain embodiments, cryogenic cooling elements may further be implemented in system 100. Tissue response to cryo-cooling and lipolysis at the target site 106 may be similar to other types of heat energy (RF, IR energy 194, for example). This is discussed further below with respect to FIG. 2.

In certain embodiments, the thermal imager 140 is configured to detect thermal energy in the infrared (IR) spectrum as a measure of the amount of energy applied to the skin at target site 106. As noted above, as the target site 106 absorbs energy 104, the surrounding tissue will increase in temperature. As the target site 106 increases in temperature, heat is radiated and manifests as IR energy, emitted from the target site 106 and detectable by the thermal imager 140. For purposes of this disclosure, IR will be considered light below the wavelength of the visible spectrum in the range of 700 nm-1 mm, or frequencies between 430 THz-300 GHz. According to the ISO (International Organization for Standardization) 20473 scheme the terms "near IR" (0.78 μm-3 μm), "mid-IR," (3 μm-50 μm), and "far IR" (50 μm-1 mm) may also be referenced herein. However, other common sub-divisions of near, mid, and far IR spectra vary and may be further sub-divided, and will be specifically referenced where stated.

The thermal imager 140 may comprise a processor ("CPU") 142 configured to execute a software program stored within a memory ("mem.") 144. The thermal imager 140 may further comprise at least one controller ("contr.") 146 operationally coupled to the processor 142 and memory 144. The thermal imager 140 may further comprise an imaging sensor ("IR") 150 operationally coupled to at least the controller 146 and configured to capture thermal images of the target site 106 and communicate the thermal images to the processor 142 and memory 144 for storage. The thermal transmitter 140 may further comprise a communications controller 152 operationally coupled to the controller 146, and configured to communicate with the analogous communications components of the thermal treatment system 100, for example, communication controller 132 of thermal transmitter 120.

The thermal imager 140 may further comprise an imaging sensor 150 operationally coupled to at least the processor 142. The imaging sensor 150 may be formed at least in part using germanium ("Ge") lenses. Ge lenses appear opaque and reflective to visible light. Ge lenses, however, may be useful in implementations for IR filtration and sensing as many Ge compound are transparent to IR light/energy. The imagining sensor 150 may be configured to sense thermal emissions from the target site 106, as discussed below. The thermal images provided to the clinician administering the thermal treatment to the patient 102 may use the thermal images as feedback, indicating where energy 104 has been applied and where energy 104 need be applied next.

In an embodiment, the thermal imager 140 may further comprise a mechanical drive 154 operationally coupled to the controller 142. In certain embodiments, the thermal imager 140 may be mounted to an autonomous system configured to adjust a field of view of an imaging sensor 150.

The imaging sensor 150 may be configured to provide precise thermal readings of the target site 106. The thermal imager 140 may be further configured to provide a high-resolution thermal reading of the target site 106 at multiple depths beneath the skin. The memory 144 may store various programs and/or algorithms that when executed by the processor 142, are configured to calculate precise measurements of the temperature of various areas at various depths below the skin surface at the target site 106. The controller 146 may use the information from the processor 142 regarding the detected thermal images (FIG. 7A-FIG. 7T) to generate commands communicated to the thermal transmitter 120 via communication link 110. These commands function as precise and timely feedback, comprising a directional adjustment or transmission level adjustment command to the thermal transmitter, based on the thermal imagery of the target site 106. In certain embodiments, the feedback provided by the thermal imager 140 is nearly instantaneous, providing optimum information for completion of the medical procedure.

The thermal imager 140, and more precisely, the communication controller 152, may transmit data regarding the thermal imagery to a communication controller 172 integrated into the thermal display 160, via communication link 110. In an embodiment, the communication link 110 may allow communication with, and projection of the thermal images and thermal data on, multiple thermal displays 160. Accordingly, in certain embodiments, one or more of the multiple displays 160 may be located apart from the thermal transmitter 120 and/or the thermal imager 140.

The thermal display 160 may comprise a processor ("CPU") 162 configured to process the data received by the communication controller 172. The thermal display 160 may further comprise a memory ("mem.") 164 operationally coupled to the processor 162 configured to store data related to data captured by the imaging sensor 150. The thermal display 160 may further comprise a controller 165 operationally coupled to the processor 162 and memory 154 and configured to control the operations of the thermal display 160. The processor 162 and controller 166 may be further configured to receive user input via a user interface 170. In an embodiment, the user interface 170 may comprise a touchscreen or display (for example, an LED display) configured to both receive input and display images captured by the thermal imager 140. The user interface 170 may further comprise a plurality of buttons, switches, or knobs.

In an embodiment, the user interface 170 may comprise a drop down menu for selection of a routine (described in FIG. 5) provided on the user interface 170. The user interface 170 may further comprise a cluster of buttons, switches or other controls located on the thermal display 160 configured to receive user input. In an embodiment, the controls may be located on the thermal transmitter 120 or the thermal imager 140.

The processor 162 and controller 166 may further be configured send data to the user interface 170, depicted as a visual representation of various temperature gradients at the targeted site 106. The user interface 170 within the thermal display 160 may provide the operator with a visual representation of both the target site 106 to which RF energy and heat is being administered as well as the surrounding area. The processor 162 may further processes the thermal reading data to generate a gradient map 200 (shown in FIG. 4) of the target site 106 and the area surrounding the targeted treatment area.

The processor 162 may be further configured to process the thermal image data to provide suggestions of additional target sites 106 or areas onto which the thermal transmitter 120 should focus to optimize the use of the RF emissions 104. The suggestions may be displayed on the user interface 170 as a plurality of arrows (not shown) indicating to the user where to direct the thermal transmitter 120. The arrows may light up on the thermal display 160, and the user may process the suggestions with the thermal image shown on the thermal display 160 to move the thermal transmitter 120.

The thermal display 160 may further include a database 174 operationally coupled to the processor 154. The database 174 may be housed within the memory 164 or may be configured as a separate component. While FIG. 1 depicts the database 160 housed within the thermal display 160, the thermal imager 140 and the thermal transmitter 120 both may have access to the information contained within the database 174 via link 110. Although not shown here, in certain embodiments, the thermal transmitter 120 or the thermal imager 140 may alternatively comprise the database 174 or comprise their own individual databases 174.

The database 174 may comprise a plurality of routines containing instructions to the system 100 to execute certain functions. The routines, when executed by the processor 164, may be configured to command movement of the thermal imager 140 (via the drive 154) to adjust focus to a different target site 106. The routines may be designed to command to the thermal transmitter 120 to adjust RF emissions and apply energy 104 to various parts of the target site 106 to optimize energy 104 exposure for a certain thermal treatment or procedure. In an embodiment, such commands or routines may be input by a clinician or other user (not shown). In certain embodiments, the system 100 may operate autonomously once a user selects a routine.

In an embodiment, routines are selected via the user interface 170. The user interface 170 may comprise a drop down menu (discussed with respect to FIG. 5) provided on the thermal display 160 that may be controlled by a touch screen or a cluster of buttons. Each routine may comprise optimum temperatures for a specific body part, which may also be cross-referenced with a specific type of treatment. For instance, one of the routines may be directed towards fat burning in which optimum heat temperatures are provided for various depths beneath the outer surface of the skin. Each routine may administer RF energy 104 differently as a result of the type of body part (target site 106) being treated. For instance, a routine which targets fat (adipose tissue) found along the abdominal area might run through heat treatments at layers 3,000-4,000 microns (or micrometers (μm)), 4,000-5,000 μm, 5,000-6,000 μm, 6,000-7,000 μm, 7,000-8,000 μm, 8,000-9,000 μm, or 9,000-10,000 μm beneath the top surface of the skin. In an embodiment, a routine may apply RF energy 104 to any depth of tissue between the surface of the skin down to 15,000 μm below the surface of the skin. Certain procedures may comprise a routine that applies energy 104 to a shallower depth beneath the for skin rejuvenation along the face. In such an embodiment, the energy 104 may be applied at depths from the surface to 1,000, 2,000, 3,000, or 4,000 μm or more (e.g., 5,000, 6,000, 7,000, 8,000, 9,000, 10,000, 11,000, 12,000, 13,000, 14,000, or 15,000 μm or more) beneath the top surface of the skin.

In an embodiment, the desired thermal treatment may comprise skin or tissue tightening at layers of the skin from the epidermis through to the reticular dermis. In another embodiment, the desired treatment may comprise fat melting or adipolysis (adipose fat digestion) in areas with high concentrations of cellulite, for example. The foregoing should not be considered an exhaustive list, as the system and devices of the disclosure may be used on any portion of the body requiring such treatment.

In an embodiment, each routine may include optimum temperatures for a specific body part, which may also be cross-referenced with a specific type of treatment. As a non-limiting example, one of the routines may be directed towards fat burning in which optimum heat temperatures are provided for various depths beneath the outer surface of the skin. Each routine may administer heat differently as a result of the type of body part, which is being treated. For instance, a routine targeting fat found along the abdominal area might run through heat treatments at layers 4,000 μm beneath the top surface of the skin, 6,000 μm beneath the top surface of the skin, as well as 10,000 μm beneath the top surface of the skin, whereas a routine directed towards skin rejuvenation along the face may only target sites 4,000 μm underneath the top surface of the skin.

The temperature range of each routine may also vary. Thus, the processors 122, 142, 162 may cooperate in order to optimize the application of thermal energy 104. In certain embodiments, the processors 122, 142, 162 and controllers 126, 146, 166 in coordination with the drives 130, 154, to command the system 100 to automatically adjust the RF emissions 104 to achieve the temperature a specific routine requires.

Many thermal treatment operations require specific temperatures at specific locations and specific depths beneath the skin. Accordingly, a high degree of accuracy and precision may be required in three dimensions to achieve the desired outcome. The various components of the system 100 may operate in conjunction, to deliver RF energy 104 to the target site 106, monitor the location and temperature of the target site 106 using the thermal imager 140, while providing timely feedback to the applicable controllers 126, 146, 166 to achieve appropriate adjustments to accomplish the desired procedure.

Figure 2:
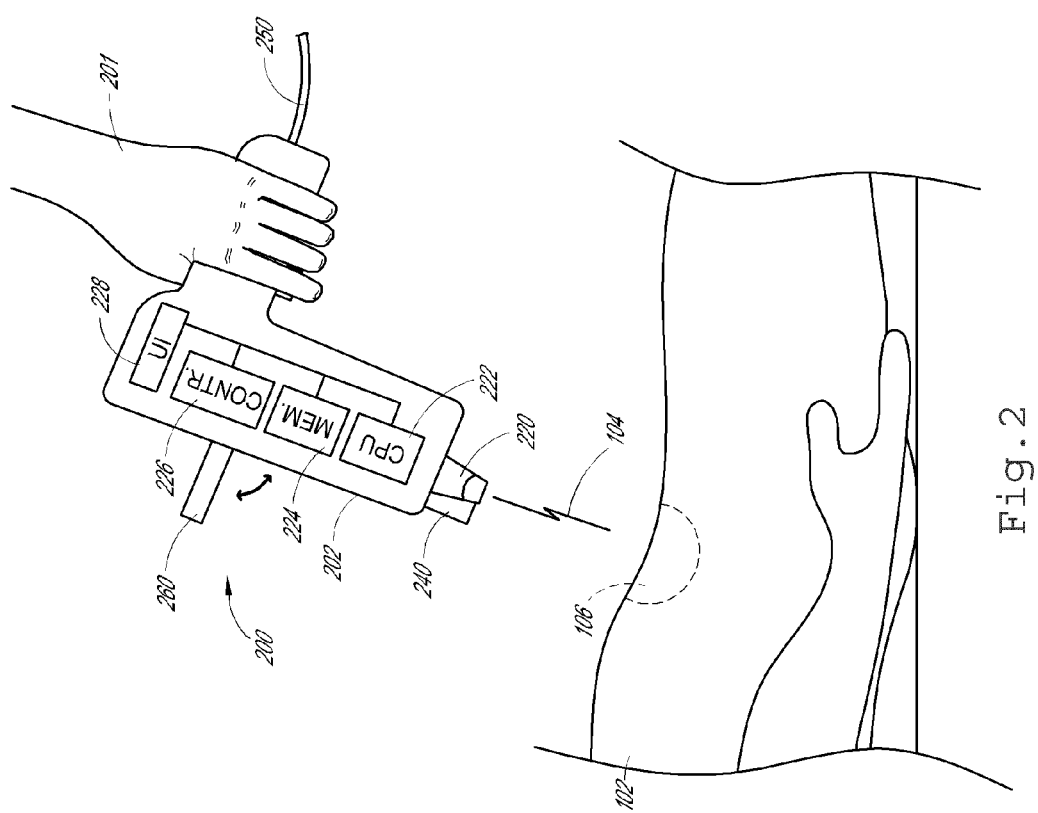
FIG. 2 is a functional block diagram of a device for application of therapeutic thermal energy according to the disclosure.

FIG. 2 shows an embodiment of a thermal treatment device 200 in accordance with the disclosure, being employed by a user 201 (also referred to herein as "operator" or "clinician") on the target site 106. In an embodiment, the thermal treatment device 200 comprises a housing 202, providing a mounting point for the various components of the thermal treatment device 200 and for protecting the internal electronics. The internal electronics are depicted here as a functional block diagram within the housing 202. The thermal treatment device 200 further comprises a thermal transmitter 220 substantially similar to the thermal transmitter 120. The thermal transmitter 220 may be configured to transmit the energy 104 toward the target site 106 (shown in dashed lines). The thermal treatment device 200 may further comprise a thermal imager 240 substantially similar to the thermal imager 140 of FIG. 1. The thermal imager 140 may sense heat emitted from the target site 106 as IR energy and provide associated thermal images and thermal data to a thermal display 260, substantially similar to thermal display 160. The thermal images displayed on the thermal display 260 may provide feedback to the user 201 for the timely adjustment of application of RF energy 104 at the target site 106, in at least direction, frequency, wavelength, and power level.

In an embodiment, the thermal display 260 is configured to provide a visual representation of readings of the thermal imager 240, providing real-time feedback to the user 201. The thermal display 260 may be mounted to a top portion of the housing 202, providing timely feedback to the user 201. The thermal display 260 may be further collapsible or deployable in a direction 208. The thermal images (shown in FIG. 7A-FIG. 7T) may indicate the areas that have already been heated with the RF energy 104 as well as those areas that have not. This may allow more precise application of RF energy 104. Some specific examples of the thermal images are discussed below with respect to FIG. 7A-FIG. 7T.

In an embodiment, the thermal display 260 may be mounted on top of the housing 202, as shown, or may be positioned on one of the sides of the housing 202 as needed for specific design requirements. In an embodiment, the device 200 may not be fitted with an integral thermal display 260 as shown, but it may be constructed or formed as an external display, similar to the thermal display 160 of the device 100 (FIG. 1).

The thermal treatment device 200 may further comprise a processor ("CPU") 222 operationally coupled to a memory ("mem.") 224. The memory 224 may store code such as an operating system, required for the proper operation of the device 200. The memory 224 may further comprise data storage for thermal images sensed by the thermal imager 240. The memory may further comprise a database analogous to database 174 (FIG. 1) containing the routines for application of thermal energy, as discussed above. The processor 222 may be configured to execute a routine or other software program configured to provide a depth of reading for the thermal imager 240.

The device 200 may further comprise a controller ("contr.") 226 operationally coupled to the processor 222 and memory 224. In an embodiment, the processor 222 may be further configured to provide suggestions to the controller 226 of areas within the target site 106 to focus the thermal transmitter 222 in accordance with the selected routine. The suggestions may comprise a plurality of arrows or other onscreen graphics depicted on the thermal display 260 indicating to the user 201 where to direct the application of RF energy 104. The arrows may light up on the thermal display 260, and the user 201 may use the suggestions with the thermal image shown to more accurately adjust application of RF energy 104 from the thermal transmitter 220. The processor 226 may further provide on-screen indication of an automatic adjustment of energy 104, or prompts indicating to the user 201 that a manual adjustment to the energy 104 output is required.

The processor 222 may further be configured to process the thermal readings so as to generate a visual representation of the target site 106 that directs the application of heat by the user 201. As a non-limiting example, in an embodiment the processor 222 may processes the thermal reading to generate a gradient map (shown in FIG. 4) of the target site 106 and the surrounding area. The gradient map may be color-coded and depicted specific temperatures of the area at the target site 106. As will be discussed below, the gradient map may depict areas that require the application of additional energy 104 as yellow, areas that have been sufficiently heated may be displayed in green, and areas are absorbing too much RF energy 104 may be displayed in red. Such a visual representation may be done at both the top surface of the skin and at various selected subcutaneous levels. Accordingly, as the user 201 is able to see by a visual indication of the heat gradient of the desired body part, the user 201 can direct the thermal treatment device 200 to the part of the body corresponding to yellow parts of the thermal display until the body part turns green, for example, on the thermal display and may reduce application or back off of a treated area in the event that it turns red on the thermal display 260.

In an embodiment, the processor 222 may use the sensory information provided by the thermal imager 240 to command the controller 226 to selectively actuate the thermal transmitter 220. Accordingly, the thermal treatment device 200 may automatically adjust (increase or reduce) the thermal transmitter 220 output according to the readings of the thermal imager 240. In an embodiment, this automatic energy reduction feature may be suitable as a safety mechanism, minimizing an excessive application of RF energy 104 and heat, while allowing the user 201 to monitor and track the thermal treatment.

In an embodiment, the controller 226 may further use information from the processor to command a RF transmitter (not shown in this figure, and substantially similar to RF transmitter 128) to adjust RF emissions 104 as needed. In an embodiment, the major components of the device 200, particularly the thermal transmitter 220, the thermal imager 240, and the thermal display 260 are substantially similar to those components in FIG. 1 providing substantially similar functions.

The feedback provided by the thermal imager 240 may be stored in the memory 204, processed by the processor 222, and output to the controller 226 which may command an adjustment to the RF output of the transmitter 220 in accordance with a selected routine. Advantageously, the increased precision of the feedback provided by the thermal imager 240 may provide the user with precise and individualized corrections, optimizing the application of the RF energy 104.

The device 200 may further comprise a link 250, operationally coupled to the processor 222, the memory 224, and the controller 226. The link 250 may provide a communication link to additional processors or a larger computer system (not shown) for the storage and use of thermal images. In an embodiment, the link 250 may further allow the processor 222 to remotely store routines (for example, the database 174 of FIG. 1) or access the additional processors to aid in processing the thermal images provided by the thermal imager 240 to provide the rapid feedback to the user 201. In another embodiment, the link 250 may further power the device 200.

In certain embodiments the link 250 may further provide the thermal images and thermal data to an external display, such as the thermal display 160 (FIG. 1). In such an embodiment, the user 201 may utilize the thermal display 260 as a feedback control, as disclosed herein, while another clinician or the patient 102 may be able to view the procedure as RF energy 104 is being applied by the user 201.

In an embodiment, the thermal transmitter 220 is configured to administer heating energy so that the skin is heated in a range between 37° Celsius and 43° Celsius at a desired depth beneath the surface of the skin. The amount of heat administered to the target site 106 may be adjusted by reducing or increasing the rate at which the heat is emitted through changing frequency or wavelength, or by increasing the magnitude of the transmission energy (for example, RF energy 104). In certain embodiments, the thermal transmitter 220, like the thermal transmitter 120, may transmit energy 104 in the RF spectrum at any frequency or range of frequencies between the ranges of 3 kHz to 300 GHz. In certain embodiments, the RF energy 104 may also be transmitted within the microwave radiation range anywhere in the range of 300 Megahertz (Mhz) to 300 GHz. Such transmissions may have wavelengths from $10^5$ meters (m) to 0.1 mm, e.g., from $10^4$ meters to 1 mm, or from $10^3$ meters to 10 mm, or from $10^2$ meters to 100 mm, or from 10 meters to 1 meter. Such wavelengths may correspond to the possible frequency bands listed herein.

In certain embodiments, the energy 104 may also be IR energy, as noted above. In an embodiment, the thermal transmitter 220 may further emit energy 104 in the form of far IR energy, falling anywhere in wavelength spectrum from 15 µm to 1 (one) millimeter (mm), e.g., from 10 µm to 0.5 mm, or from 1 µm to 0.1 mm.

In an embodiment implementing a cooling element, as noted above in FIG. 1, a reduction in temperature of tissue at the target site 106 may be accomplished by a cooling element or elements (not shown) comprising a cooling element affixed to the distal end of the thermal transmitter 220. The cooling element may comprise a refrigerant- or water-cooled element that may be in contact with the skin at the target site 106. A supply for the cooling element may be situated external to the device 200, with a link 250 configured to supply a circulating coolant through the portion of the thermal transmitter 220 in contact with the tissue at the target site 106. Various illustrations of such an embodiment are depicted in FIG. 7A-FIG. 7T. As noted previously, the cooling elements may provide cooling of the tissue for lipolysis/adipolysis or for topical skin cooling at the target site 106, reducing the potential for superficial burns from the energy 104.

Figure 3:
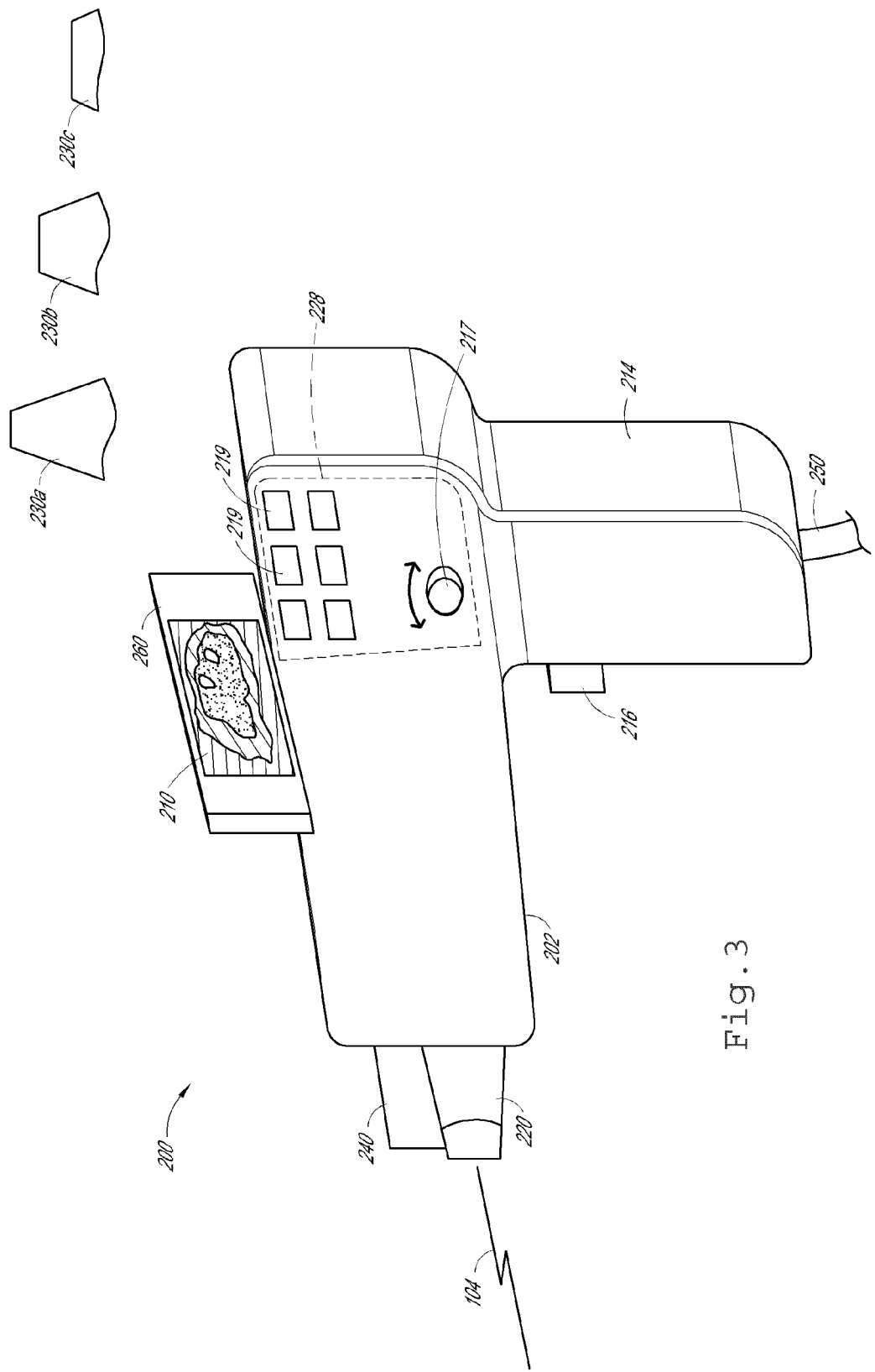
FIG. 3 is a close up functional block diagram of the device of FIG. 2, according to the disclosure.

FIG. 3 shows another view of device 200, with the thermal display 260 is illustratively shown deployed, providing a gradient map 210 showing the thermal gradient of a body part (for example, the target site 106) treated by the thermal treatment device 200. Though FIG. 2 shows the thermal treatment device 200 used on the abdomen of a patient, it should be appreciated that the thermal treatment device 200 may be used on other body parts as needed, such as the face, legs, neck, and arms.

The thermal treatment device 200 may both transmit thermal energy as RF emissions 104 to the target site 106 as well as map the thermal readings sensed by the thermal imager 240 at the target site 106. Thus, the operator 201 is able to manually adjust the application of RF energy 104 along the target site 106 so as to achieve a desired temperature. In some embodiments, to accomplish a desired routine, the temperature across the target site 106 may need to be substantially uniform. The thermal imagery and feedback to the user may enable a substantially uniform distribution of RF energy 104 and heat across the target site 106.

In an embodiment, the thermal imager 240 may provide thermal readings at multiple levels beneath the surface of the skin, displayable on the thermal display 260. By manipulating the user interface 228, the user may display one or more of the various readings, from, for example the temperature of the top surface of the skin (epidermis) may be provided, or the temperature of a predetermined depth of the body part at the target site 106 may be provided. Accordingly, the user is given real-time feedback with regard to achieving a desired temperature for a process such as lipid burning, while maintaining awareness of the temperature of the target site and considering the patient's 102 comfort level and the risk of burns.

The housing 202 may further include a grip portion 214 configured to be gripped for one-handed operation. An end portion of the housing 202 may be adapted to secure the thermal transmitter 220 as shown. The thermal display 260 is shown mounted to a top surface of the housing 202. In an embodiment, the thermal display 260 may be constructed on a hinge mount, allowing it to deploy or fold in the direction 208 (FIG. 2) or pivot about a vertical axis (not shown).

The device 200 may further comprise an actuator 216. The actuator 216 may be a button or a switch operationally coupled to the controller 226 and configured to actuate both the thermal imager 240 and thermal transmitter 220. The thermal imager 240 and thermal transmitter 220 may be actuated simultaneously. In another embodiment, the device 200 may include individual actuators 216 (not shown), each configured to actuate the thermal imager 240 or thermal transmitter 220.

In an embodiment, the thermal transmitter 220 may comprise a variable actuator 217 allowing manual adjustment or tuning of the RF energy 104 transmitted by the thermal transmitter 220. The variable actuator 217 may adjust the frequency, wavelength, power, phase, and/or amplitude of the emitted RF energy 104. The functions of the variable actuator 217 may be further augmented by other portions of the user interface 228, depicted in FIG. 3 as the variable actuator 217 and a series of buttons 219. The actuators 216 may also be considered part of the user interface 228. While the thermal transmitter 220 is illustratively described herein as an RF emitter, certain embodiments of device 200 may be adapted to emit thermal energy in other forms such as laser, ultrasound, or the like.

The thermal treatment device 200 may further comprise a plurality of tips 230 applied over the thermal transmitter 220. Each thermal tip 230 may be predesigned and optimized for applying a specific type and amount of energy to a specific depth of skin. In an embodiment, each tip 230 is configured to apply thermal energy at a predetermined depth from the top layer of a patient's skin (shown in FIG. 2). As a non-limiting example, tip 230a may provide thermal treatment at a depth of 4,000 microns (or micrometers (µm)) beneath the top surface (epidermis) of the skin, whereas tip 230b may be configured to provide thermal treatment at 6,000 µm beneath the top surface of the skin, and tip 230c may be configured to provide thermal treatment at 10,000 µm beneath the top surface of the skin. Each tip 230 may direct the energy at a specific pattern, frequency, wavelength, or magnitude for proper application of heating energy to the skin. In an embodiment, the device 200 may comprise the tips 230 may operate in lieu of the actuators 216, 217. In an embodiment, the tips 230 may operate in conjunction with the actuators 216, 217, providing some degree of adjustment within the design specifications of the tips 230a.

In an embodiment, the thermal imager 240 is configured to provide a high-resolution thermal reading of an application area along multiple depths beneath the skin. The thermal imager 24 transmits its readings, or images, to the a processor 222 (FIG. 2) and to the thermal display 260 to provide the user with a visual representation of the heating energy absorbed by the skin, both at the target site 106 in addition to the surrounding area.

The device 200 is illustratively shown having tip 230b installed, so as to administer heat at a depth of 6,000 µm underneath the surface of the skin. It should be appreciated, that the delivery of heat at that depth may also administer heat at the layers between the top surface of the skin and the optimized depth. Further, it should be appreciated that the application of RF energy 104 and heat may depend upon the physical characteristics of the body part (for example, target site 106) being treated. As a non-limiting example, a subcutaneous area covered by a scar or a birthmark may take longer to reach an optimal temperature as the energy 104 may be absorbed by the scar or birthmark instead of the skin beneath. Accordingly, the patient 102 may feel discomfort at the site of the birthmark, prior to achieving a desired temperature at the subcutaneous level.

As the device 200 is actuated, the thermal transmitter 220 may apply energy 104 and heat to the target site 106 which is simultaneously sensed by the thermal imager 240 and mapped to the thermal display 260. The gradient map 210 may be configured to show an absolute temperature of the skin (target site 106) at different levels beneath the surface. In an embodiment, one display setting may depict the temperature of the surface of the skin on the thermal display 260, and in another setting, the temperature at the targeted depth of the body part may be provided on the thermal display 260.

For illustrative purposes, assume that the operator 201 (FIG. 2) has selected a routine for controlling the actuation of the thermal treatment device 200 as applied to the target site, for example, the abdomen as shown in FIG. 1 and FIG. 2. The processor 222 may execute a program to vary the reading of the thermal imager 240 at a depth of 6,000 μm and at the surface of the abdomen. For illustrative purposes, 6,000 μm below the surface of the skin may be the location where most lipids are found on the patient 102. The tip 230b is selected to provide heat treatment at 6,000 μm below the surface of the skin. Accordingly the thermal display 260 is activated and will provide a thermal image of both the top layer of the skin at the target site 106 as well as the targeted depth (6,000 μm) of heat application. The user may monitor the results of the heat treatment on the thermal display 260, and may manually adjust the output of the thermal transmitter 220 so as to achieve a desired temperature both at the top surface and subsurface levels. The user may also manually direct the thermal treatment device 200 so as to deliver energy 104 and heat to areas that have no yet reached the desired temperature at the subcutaneous level, while simultaneously keeping heat from being administered at certain top surfaces of the abdomen.

In another embodiment, the processor 222 may gather thermal readings from the thermal imager 240 to automatically control the transmission of the thermal transmitter 220 so as to achieve a desired temperature at the subcutaneous level while preventing discomfort to the patient at the topical level.

Figures 4, 5:
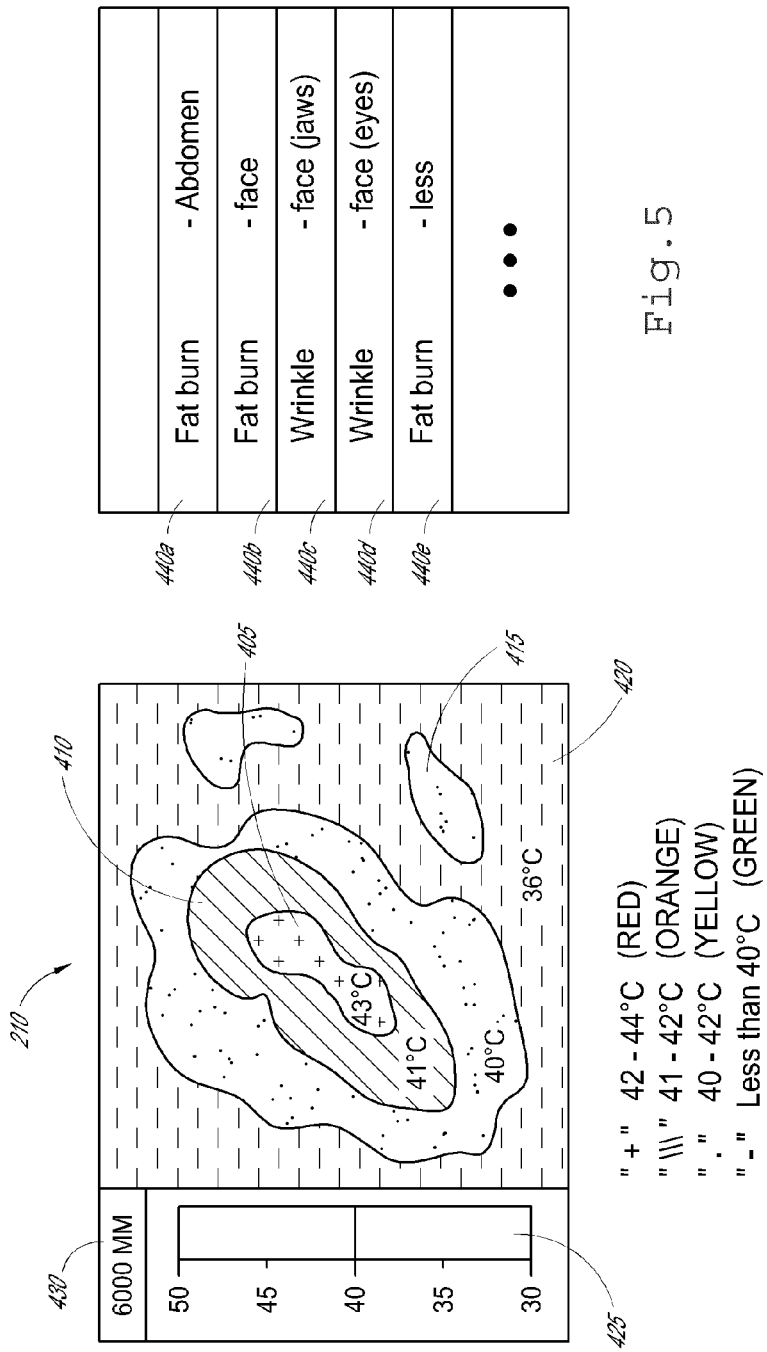
FIG. 4 is a functional block diagram of a user interface, according to the disclosure.
FIG. 5 is functional block diagram of a thermal display according to the disclosure.

FIG. 4 shows a diagram of the gradient map 210 (FIG. 3) displaying thermal gradients resulting from data collected by the thermal imager 240, 140. As noted above, the gradient map 210 may provide a user timely and precise feedback regarding the application of energy 104 to the target site 106. In an embodiment, the gradient may be color-coded. For purposes of this discussion, the range of temperatures less than 40° C. may be colored green 420, areas from 40° C.-42° C. are colored yellow 415, areas from 41° C.-42° C. are colored orange, and areas from 42° C.-44° C. and higher may be colored red. The gradient map 210 may further have a gradient key 425 indicating the temperatures as represented by the colors in the gradient. The gradient map 210 is intended to provide a visual indication of what areas within the target site 106 have achieved the optimum temperature according to a selected routine, and those that are not, such that the user 201 may adjust the energy 104 as needed. It is to be appreciated that each of the colors may be selected based on user 201 (FIG. 2) and device 200 requirements. It should also be appreciated that the specific scale shown in FIG. 4 is a non-limiting example of temperature ranges. The scale colors and values may be adjusted as desired.

Accordingly, as the user 201 is able to see by a visual indication of the heat gradient of the desired body part or target site 106, the user 201 can move the thermal transmitter 220 to the part of the body corresponding to the appropriate colors depicted in the gradient map 210. As non-limiting example, the user 201 or clinician may concentrate energy 104 on certain yellow parts of the gradient map 210 until that body part (for example, the target site) turns orange on the thermal display 260 and may decrease the energy 104 in a treated area in the event that it turns red.

In an embodiment, the colors are not limited to four distinct colors but to a constant spectrum from purple or black, for example, designating a cold (for example, below 37° C.) region through the visible light spectrum to red (for example, hot). Accordingly, a central color such as orange (as shown) or green may be selected as the color representing an "optimum" temperature for the selected routine.

In another embodiment, the absolute temperature of the target site 106 may further be displayed on the gradient map, as shown, in addition to the depth reading 430. In another embodiment, a different gradient map 210 may be selected and displayed for a given skin depth 430.

FIG. 5 depicts a selection screen 400 that may be displayed on the user interfaces 170, 228, showing several possible user-selectable routines 440a-440e that may be chosen via the user interface 228. As shown, routine 440a may be selected for a fat burning process on the abdomen requiring a first energy 104 frequency (and wavelength) and depth setting. Routine 440b may be a fat burning process on the face possible requiring a less powerful routine than routine 440a. Routine 440c for wrinkle removal and skin tightening on the face and jaws or routine 440d for wrinkle removal around the eyes may require a lower setting still for a different amount of time. Routine 440e may be directed to a program or routine configured to address the areas that are heated to a lesser degree than others ("-less"). In the routine 440e, the user 201 may be directed to apply RF energy 104 to equalize the temperature applied across the target site 106 in a uniform manner. Advantageously, this may lead to an increase in the uniformity of skin heating across the target site 106 and reduction of heat "cavitation," leading to irregularities and inconsistent results. "Cavitation" as used here refers to irregular, or non-uniform heating.

Figure 6:
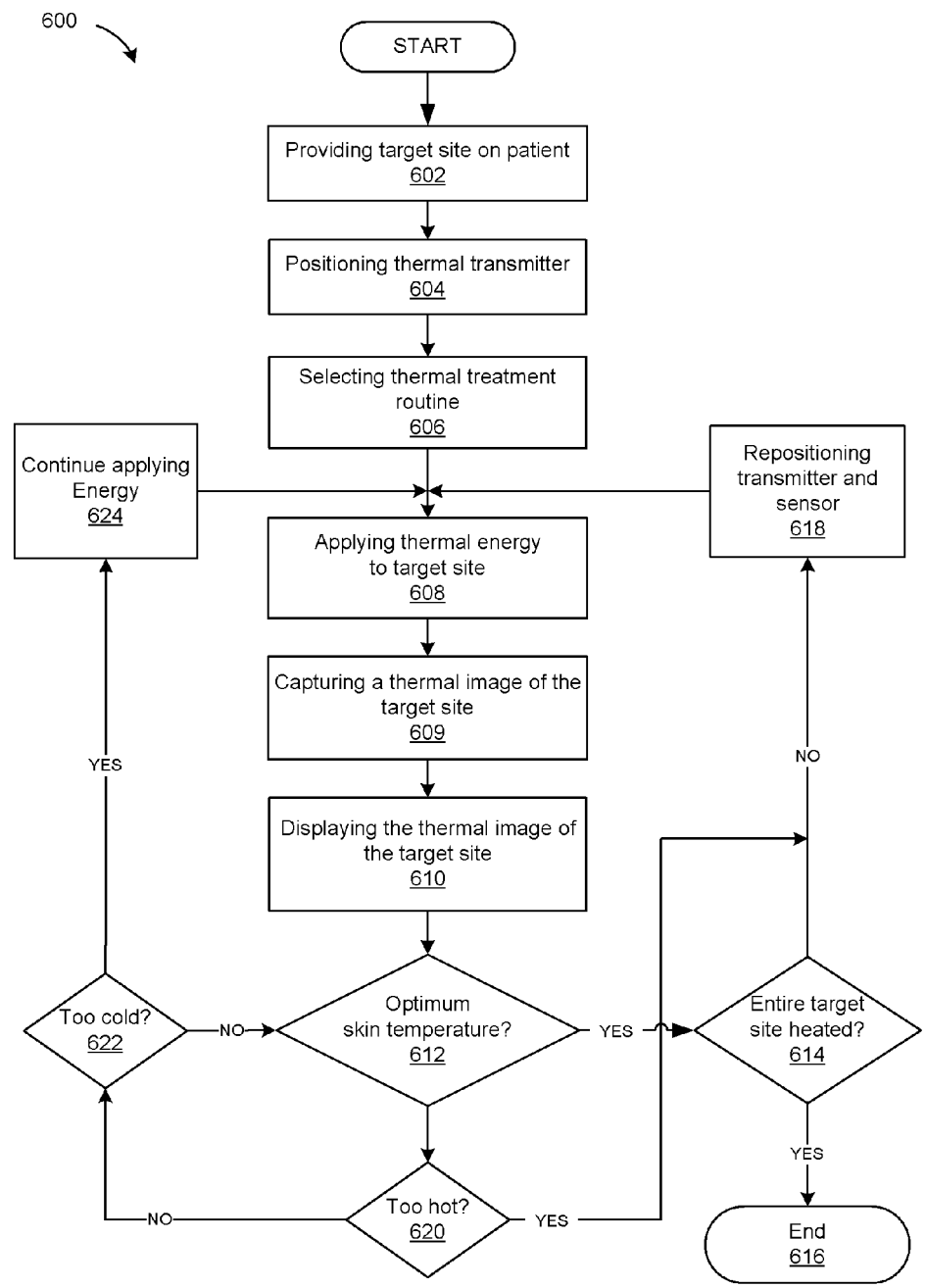
FIG. 6 is a flowchart depicting a thermal feedback process according to the disclosure.

FIG. 6 shows a flowchart depicting a method 600 for providing feedback in a thermal treatment device according to the disclosure. In an embodiment, the method 600 begins with block 602 where a target site 106 on the patient 102 is provided. In an embodiment, the target site 106 may be an area on the abdomen where the patient 102 desires to reduce the amount of fat present. Alternatively, the target site may be a more sensitive area (such as the eyes) where the patient 102 desires a skin tightening procedure.

At block 604, a clinician 201 may position the thermal transmitter 120, 220, and direct it toward the target site 106. At block 606, the clinician 201 may select and initiate a desired thermal treatment routine. Once the thermal treatment routine has been initiated, at block 608 the thermal transmitter 120, 220 may apply RF energy 104 to the target site 106.

In an embodiment, at block 609, the thermal imager 140, 240 may capture thermal images of the target site 106 as RF energy 104 is absorbed by the tissue at the target site 106 and display the thermal images on the thermal display 160, 260. The thermal imager 140, 240 may make use of germanium lenses or other thermal detection technologies for the detection and capture of thermal images of the target site 106. In certain embodiments, forward-looking infrared technology (FLIR) and CCD (charge-coupled device) cameras capable of capturing thermal images may also be implemented for such a purpose. The processor 142, 242 may use the communications controller 146 to communicate the images as feedback to the thermal display 160, 260 for processing and display on the user interface, 170, 226 at block 610. In certain embodiments, some of the processing may be carried out locally within the processor 122, 142 at the thermal imager 140, 240. In an embodiment, the processor 162 may, according to the selected routine stored within the database 174, determine that the optimum temperature has been reached at the target site 106. The optimum temperature may be at the surface of the skin, below the surface of the skin, or fall within a range of temperatures according to the routine. If that optimum temperature is reached, at decision block 614, the processor 162 may determine whether there is further tissue within the target site requiring treatment or the process requires the optimum temperature be maintained for a particular amount of time. If the routine has completed, then the method 600 ends at block 616.

At decision block 614, when the processor 162 determines there are further areas requiring thermal treatment, the controller 162 may command the thermal transmitter 120 to adjust aim at block 618 and move the RF energy 104 to a different location. The controller 162 may further command the thermal imager 140 to adjust the field of view. In the event the device 200 is being employed, the processor 222 may determine that the adjustment is required and indicate to the clinician 201 on the thermal display 260 where to apply the RF energy 104 and whether and how much the energy 104 may have to be adjusted in power output and/or frequency/wavelength. The method 600 may then return to block 608 and apply energy 104 to the target site 106 at block.

At decision block 612, if the target site 106 is not at the optimum temperature, the processor 162 may determine if the temperature is too hot (decision block 620) or too cold (decision block 622) according to the routine and database 174. If the target site is too hot, the processor 162 may determine that the aim point of the thermal transmitter 120 needs to be moved and proceeds to block 618. The method 100 may then proceed as explained above.

At decision block 622, if the target site is too cold, then the processor 162 may indicate that more energy 104 is required for the routine. In an embodiment, if the clinician is using device 200, then the thermal imagery displayed on thermal display 260 may indicate colors and temperatures indicating a target site 106 that is still too cold, according to the routine. The routine may then require additional energy applied to the target site 106, as the method 600 returns to block 608 and proceeds as noted above.

FIG. 7A-FIG. 7T are thermal images from a thermal treatment procedure according to the present disclosure. FIG. 7A shows a thermal image 710 of a clinician 712 applying RF energy 104 to a patient 102 with a thermal treatment device 700 (FIG. 7B), similar to that discussed above. The device 700 may be analogous to the device 100 as discussed above. FIG. 7A shows a thermal image 710 that may be representative of the thermal information displayed on thermal display 160, 260 for use by the clinician 712 or by the controllers as feedback to conduct the treatment procedure. The thermal image 710 depicts the absorption of thermal energy 104 by the target site 106 with the lighter colors (white) designating the areas that have been heated. The thermal image 710 may be further superimposed with the thermal gradient such as in the gradient map 210. The "measurements" indicated on the figures corresponds to the temperature of the target site within the box, "Ar1," designating target "area" one. Subsequent figures depict multiple "Ar's" (for example, Ar1, Ar2, Ar3) that may be used to indicate various ranges within the gradient map 210. In some figures, an "El1" may be utilized for the same purpose, The various features of the gradient map 210 depicted in FIG. 4 may be further added to the thermal image 710 to provide further information and feedback to the clinician 712.

As shown in the subsequent images in FIG. 7B-FIG. 7T, the clinician 712 may move the device 700 in various locations to complete the procedure or routine 440 as discussed herein. The thermal images 710 and constant feedback from the application of the energy 104 to the patient 102 may optimize the procedures by providing the clinician 712 with a visual and qualitative representation of where energy 104 has been applied and where it has not. The "measurements" depicted in the thermal images 710 of FIG. 7A-FIG. 7T further provide a quantitative indication of the skin heating allowing the clinician 712 to more accurately and efficiently direct the thermal treatment. The "Max," "Min," and "Average" notations in the "Measurements" box refer to the relative temperatures within the designated area Ar1, as shown, for example, in FIG. 7A. FIG. 7G depicts multiple areas Ar1-Ar3 and the associated temperatures. An area El1, shown in FIG. 7B depicts a similar range of temperatures, indicating to the clinician 712 various temperature measurements at the target site 106.

Figure 8:
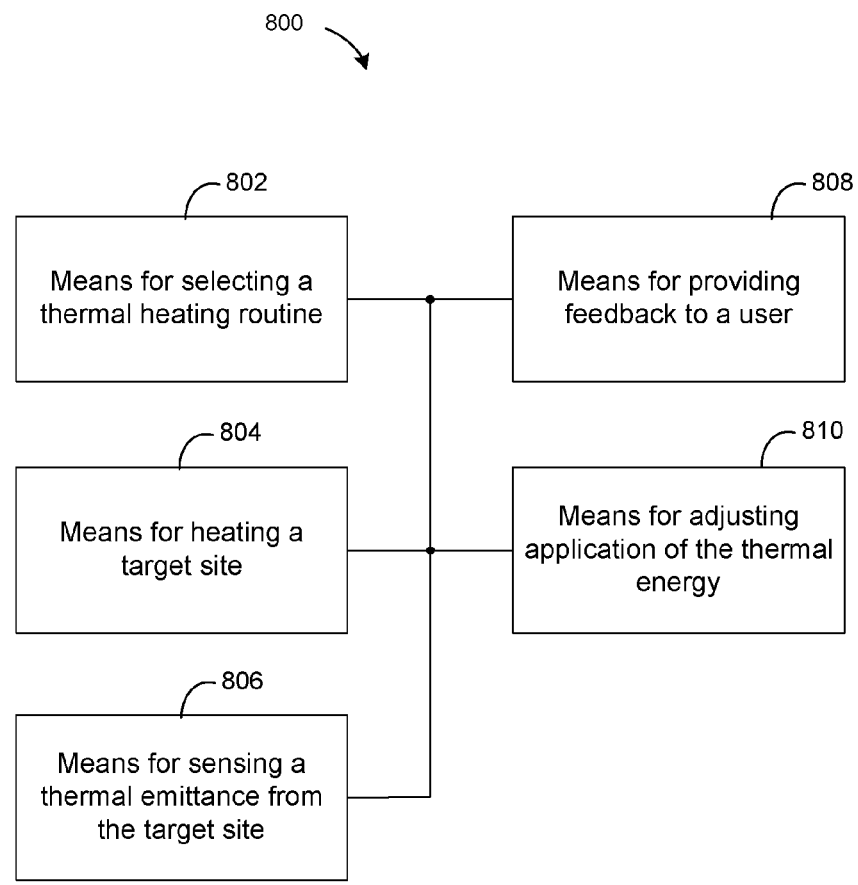
FIG. 8 depicts a functional block diagram of an embodiment of the thermal treatment device according to the disclosure.

FIG. 8 depicts a functional block diagram of an embodiment according the disclosure, referred to as a thermal treatment device 800. The device 800 comprises a means for selecting a thermal heating routine 802. The means for selecting a heating routine may be configured to allow a user 201 to select a specific target site 106 around the abdomen or other area as required. The routine may provide details as to how much thermal energy is required at the target site 106 and how to adjust the application of the energy 104 in response to feedback from a means for sensing the thermal emittance (discussed below).

The means for selecting the selecting a thermal heating routine 802 is operationally coupled to means for heating a target site 804, according to the selected routine 440. The means for heating a target site 804 may further direct energy 104 to the target site 106 according to user 201 input.

The device 800 may further comprise means for sensing thermal emittance 806. As energy 104 is absorbed by the target site 106, the target site 106 will radiate or otherwise emit IR energy that may be captured by the means for sensing thermal emittance 806. The means for sensing thermal emittance 806 may then feed the associated thermal information back as thermals images and specific temperatures at selected skin depths to a means for providing feedback to a user 808. The means for providing feedback to a user 808 may comprise a display, as noted above, depicting a gradient map indicating the portions of the target site 106 that have been heated. The means for providing feedback to a user 808 may further indicate portions of the target site 106 that require further application of energy 104, in accordance with the selected routine 440.

The device 800 may further comprise means for adjusting application of thermal energy to the target site 810. The means for adjusting application of thermal energy 810 may use the feedback provided by the means for providing feedback 808 to adjust the output of the means for heating a target site 804 in order to comply with the requirements of the selected routine 440.

A hand-held apparatus can be conveniently employed for administering treatment in certain embodiments. In other embodiments, it can be advantageous to employ a pod, bed, booth, canopy, or other structure including one or more of the components of the systems as described herein to administer treatment.

Figure 9:
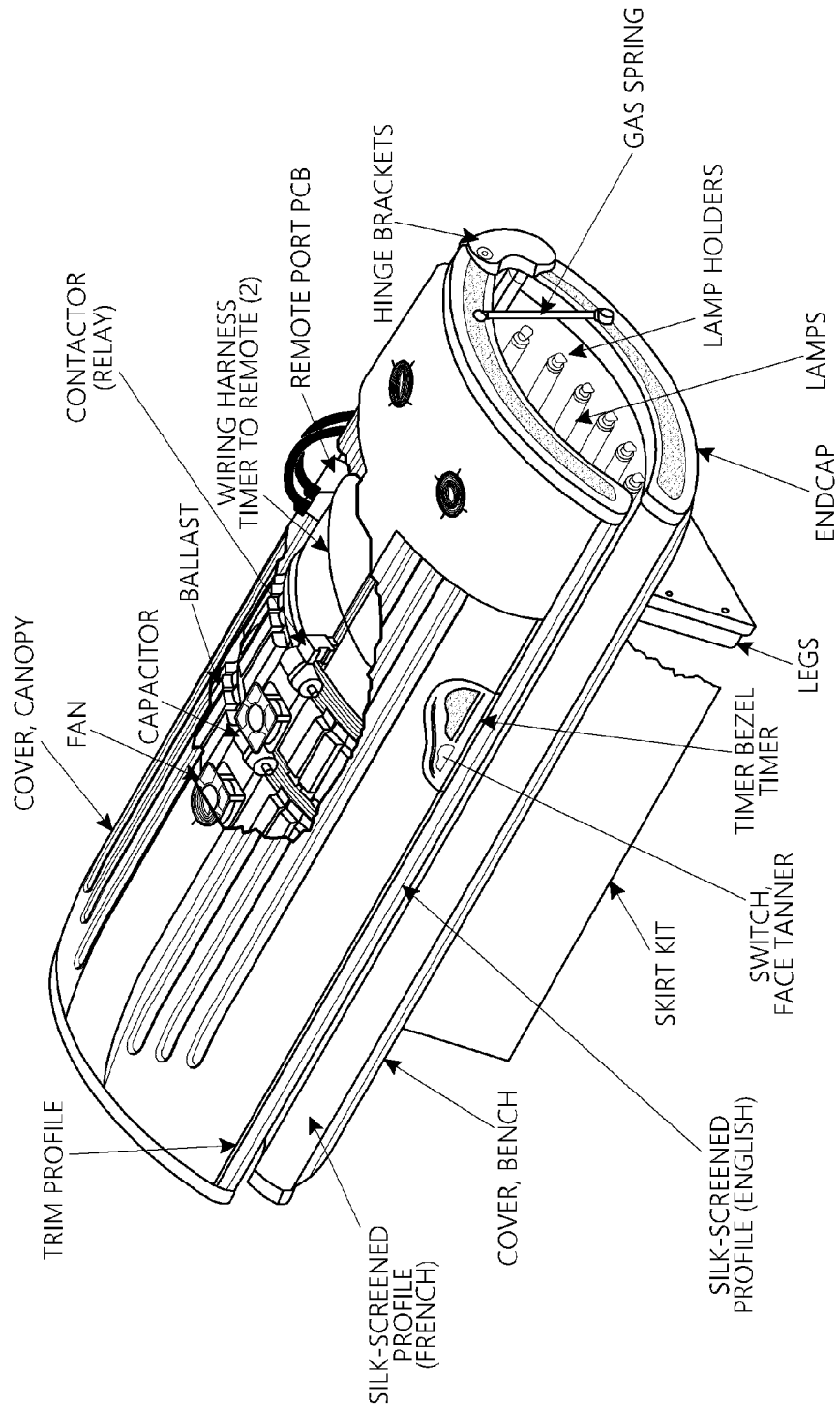
FIG. 9 depicts a bed or pod adaptable for administering thermal treatment according to the disclosure.

In one embodiment, the thermal treatment is administered by use of a bed or a pod similar in design to a conventional tanning bed. FIG. 9 depicts the SUNVISION 28LE2F, a conventional tanning bed including various components: a cover or canopy, a fan, a capacitor, a ballast, a contactor or relay, wiring harness timer to remote, remote port PCB, hinge brackets, a gas spring, lamp holders, lamps, endcap, legs, timer bezel and timer, switch, face tanner, skirt kit, silk-screened profile, cover or bench, and trim profile. The bed or pod can provide coverage of any portion of the patient's body. For example, in a bed configuration, the patient lies on the bed (e.g., face up, face down, or any other position), and emitters in the bed apply energy to a body part adjacent to the surface of the bed. The surface on which the patient is placed is transmissive to the radiation, e.g., holes or other ingresses provide passage therethrough for the energy, or the surface is fabricated from a material that is at least partially transmissive to the radiation. In another design, the patient lies on a bed or other surface, and a frame, canopy, or other structure incorporating one or more emitters is placed over the patient. Alternatively, a pod or booth in which the patient stands is provided, and one or more emitters arrayed in the pod or booth administer the energy while the patient is standing. Systems employed for application of radiation, or UV light, can be adapted to similarly administer energy as in the methods of the embodiment.

Such a bed or pod design can be adapted for use in the methods of the embodiments by substituting one or more emitters as described herein for conventional UV lamps. The emitters can be of the same or different type, and configured to deliver the same or different energy (RF, heat, light, microwave, or ultrasonic). When multiple emitters are employed, they can be arranged in any suitable configuration, e.g., an array of 2 or more emitters, e.g., 2, 3, 4, 5, 6, 7, 8, 9, or 10 to 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 emitters. The emitters can be arrayed in a grid (e.g., square, triangular, offset rows, random) and can be individually actuated to deliver a desired radiation profile (wavelength, frequency, total energy delivered, power, continuous, intermittent, or any other desired variation) to targeted areas of the patient's body. The emitters can be stationary, or can be configured to be movable within the device so as to provide a desired energy profile to the patient. In an embodiment employing one emitter, it can be desirable to employ a moveable emitter. Such a moveable emitter can be one that moves in a fixed path along a track in the device, or can be incorporated into a robotic positioning system configured to move the emitter in three dimensions over the patient's body.

The bed can be further equipped with one or more thermal cameras or visible wavelength cameras. The one or more cameras can be positioned in the bed or pod so as to provide coverage of portions of the patient's body, or the entirety of the patient's body. Advantageously, the cameras can be integrated into the bed or pod between the emitters. Images from one or more of the cameras, e.g., a thermal camera or visible light camera, can be processed, e.g., by a microprocessor or other computer implementing pattern recognition software as part of the overall treatment system, to determine the positioning, size, shape, and topography of the patient. This information can be used to generate a 3-dimensional construct that can be employed by the system to select the desired operating parameters of the emitters adjacent to the area(s) of the patient's body to be treated, e.g., while treatment is in progress, so as to account for movement of the patient, or to deactivate emitters that are not positioned over a portion of the patient due to the patient's positioning or size. The thermal cameras can also be employed to provide feedback regarding patient temperature at various locations which can be employed to adjust emitter operating conditions, e.g., to increase, decrease, start, stop, or otherwise adjust some aspect of the energy being delivered to the patient.

In certain embodiments, it may be desirable to immobilize the patient during treatment. Suitable apparatus can be provided, as is employed in other imaging technologies, so as to position and/or immobilize one or more areas of the body to be treated, e.g., frames, clamps, bindings, etc.

The treatment system can include a microprocessor or other computer built into the bed or pod to perform one or more of the computing functions described herein, or a microprocessor or other computer can be connected via a wired connection or wirelessly to the bed to control processes. A single processing system can be employed, or a plurality of processing systems can be employed that perform different tasks.

In one embodiment, a system utilizing a pod, bed, or booth is configured to provide an assessment of a patient's fat. Cameras can be employed to create a three-dimensional construct of the patient that can be analyzed to determine fat-bearing areas to be targeted for treatment. The system then uses this information to determine a treatment protocol. The treatment is administered, with adjustments to the treatment protocol made using feedback from one or more sensors, e.g., thermal imaging cameras that detects the extent to which fat is burned. When a desired degree of fat burning is detected, then the treatment is ended. The one or more cameras can also be employed to determine positioning of the patient, e.g., to compensate for movement. The system can advantageously employ one or more motors and associated systems that move the one or more transmitters (and/or one or more cameras or sensors) around the patient, e.g., while assessing fat. The moving parts of the system can advantageously be placed such that they do not contact the patient's body, e.g., behind a transmissive structure, e.g., a polymer window, a polymer or metal grid, or other structure.

Figure 10:
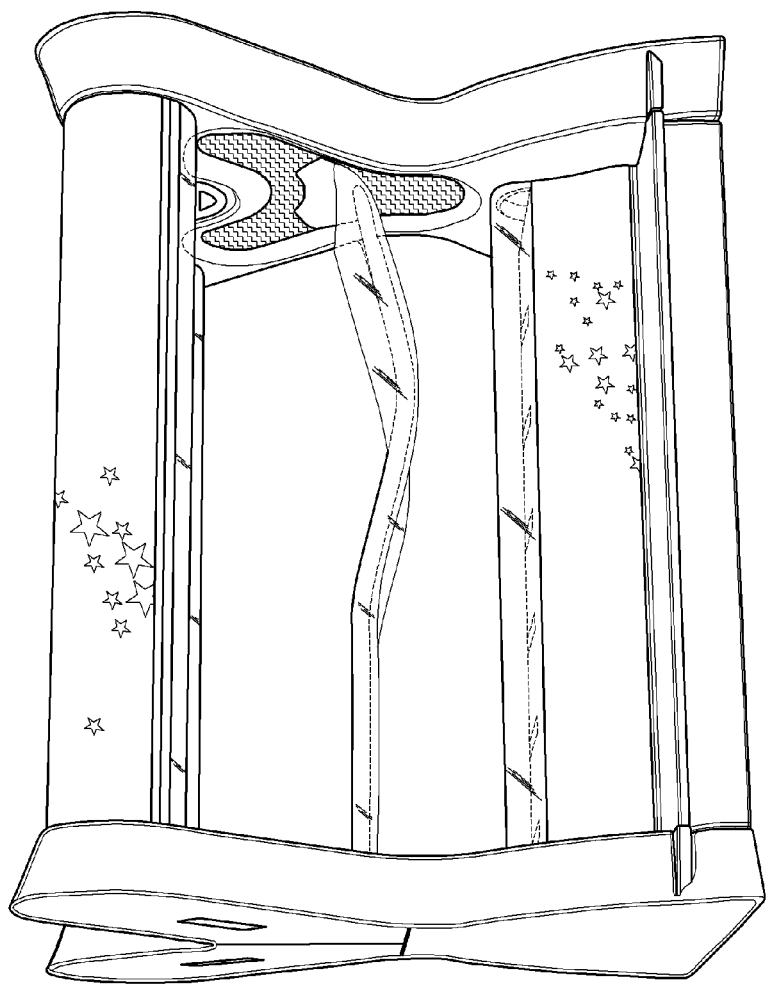
FIG. 10 depicts a commercial tanning bed adaptable to deliver thermal treatment as in the various embodiments.
Figure 11:
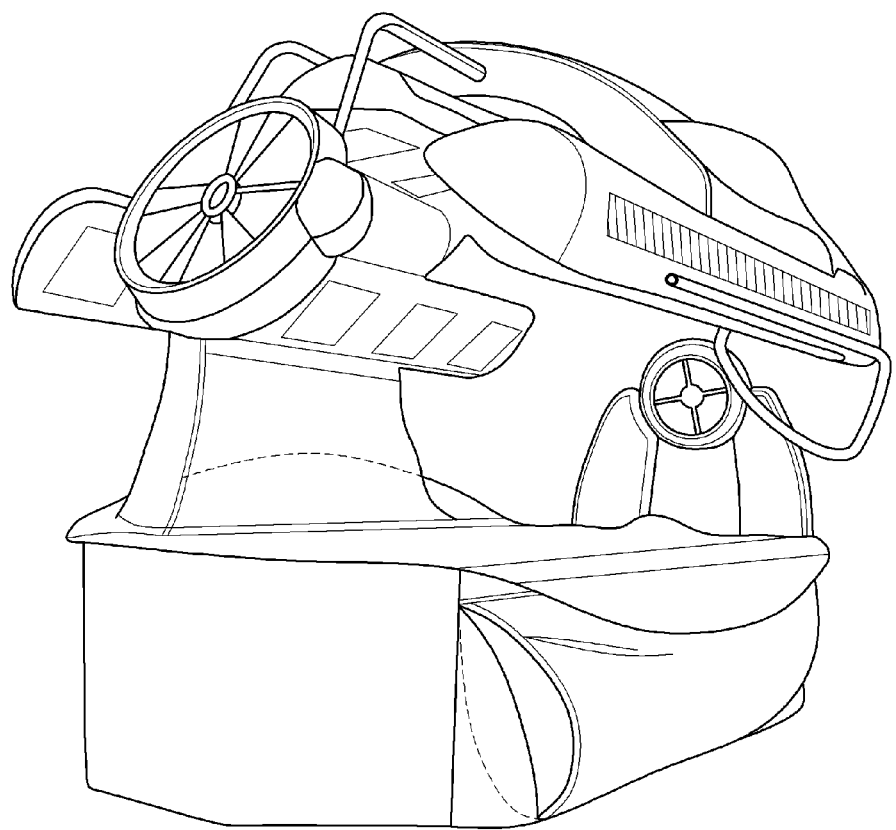
FIG. 11 depicts a commercial tanning bed adaptable to deliver thermal treatment as in the various embodiments.
Figure 12:
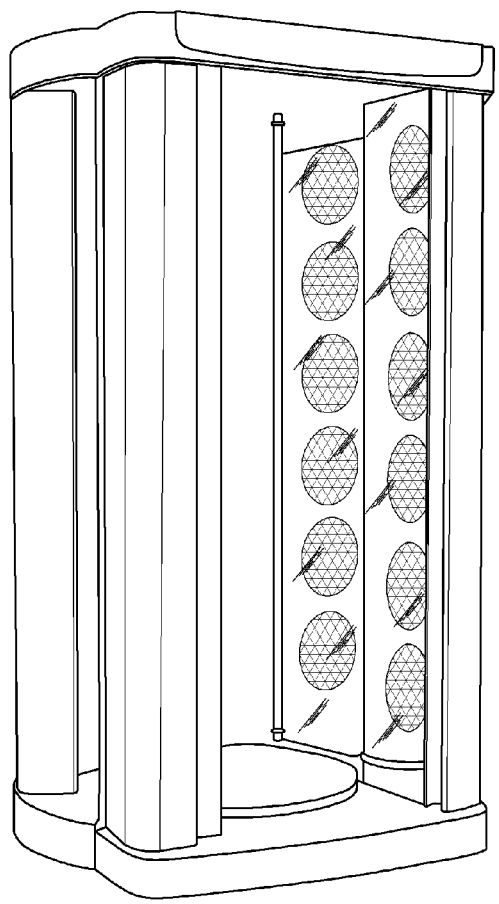
FIG. 12 depicts a commercial tanning booth adaptable to deliver thermal treatment as in the various embodiments.
Figure 13:
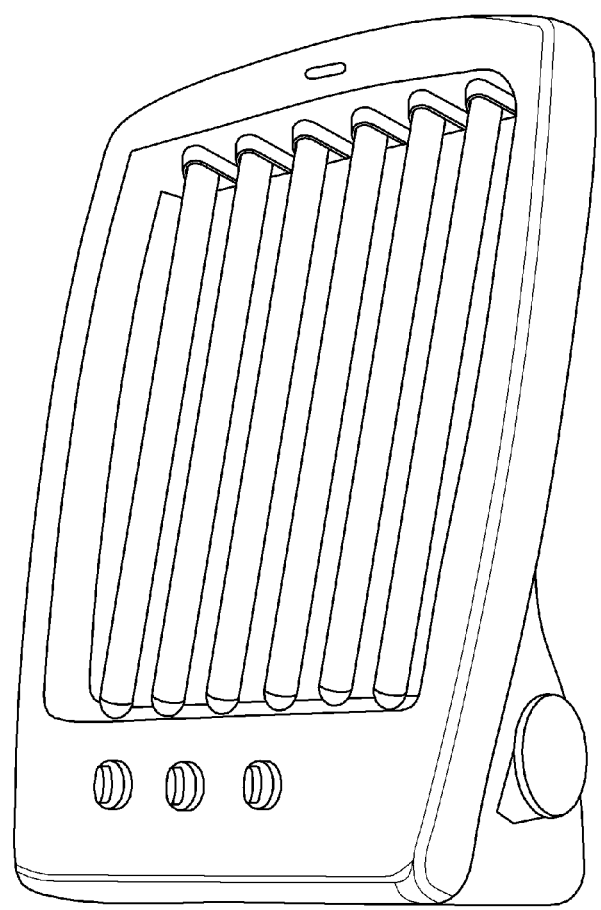
FIG. 13 depicts a commercial facial tanning device adaptable to deliver thermal treatment as in the various embodiments.

FIGS. 10-12 provide images of commercial tanning beds. A similar configuration can be adapted for use with the transmitters of preferred embodiments.

While this invention has been described in connection with what are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged, or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Thus, while the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any thermal treatment system. It should further be appreciated that the implementation and/or execution of all methods and processes may be performed by any suitable devices or systems, whether local or remote. Further, any combination of devices or systems may be used to implement the present methods and processes.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure, and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A thermal treatment system, comprising:
   a pod configured for housing a body part of a patient;
   a member for immobilizing the body part;
   a thermal transmitter on the inside surface of the pod, the thermal transmitter configured to apply an amount of radiofrequency energy or microwave energy to a target site located below the surface of the patient's skin of the patient body part up to 15,000 micrometers below the surface of the patient's skin, the radiofrequency energy or microwave energy configured to heat the target site to a first temperature while the surface of the patient's skin has a second temperature lower than the first temperature, the first temperature is between about 35 degrees Celsius and about 50 degrees Celsius, and the second temperature does not damage the surface of the patient's skin;
   a thermal imager on the inside surface of the pod, the thermal imager configured to capture thermal data and thermal images at any location depth selected from about 15,000 micrometers below the surface of the patient's skin to the surface of the patient's skin including both the the target site and tissue surrounding target site;
   a processor operably connected to the thermal transmitter and the thermal imager, the processor configured for receiving captured thermal data and thermal images of the target site;
   a controller operably coupled to the processor and configured such that the amount of radiofrequency energy or microwave energy from the thermal transmitter is adjustable by the controller and processor with respect to frequency and wavelength, or power level;
   a mechanical drive mechanically coupled to the thermal transmitter and operably coupled to the controller such that the mechanical drive is configured to receive commands from the controller to adjust a direction of the applied radiofrequency energy or microwave energy; and
   wherein the thermal transmitter and the processor are configured for ending application of the radiofrequency or microwave energy from the thermal transmitter after an elapsed time.

2. The system of claim 1, further comprising:
   a user interface allowing a selection of a routine for the application of the radiofrequency or microwave energy to the target site, the routine comprising instructions for the application of the radiofrequency energy or microwave energy;
   the processor configured to process the captured thermal images and thermal data according to the selected routine;
   a thermal display configured to display the thermal data and the thermal images; and
   the controller configured to indicate on the thermal display a required adjustment to the frequency or wavelength and the power level of the thermal transmitter, or command an adjustment to the frequency or wavelength and the power level of the thermal transmitter, based on the thermal data and the thermal images, according to the selected routine.

3. The system of claim 2, further comprising a memory configured to store information related to the execution of the selected routine, accessible by the processor, the thermal transmitter, and the thermal imager, the memory further comprising at least one database for storing a plurality of routines.

4. The system of claim 2, further comprising a wireless communication link operationally connecting the thermal transmitter, the thermal imager, and the thermal display.

5. The system of claim 2, wherein the thermal display is configured to display the thermal images and a gradient map, and wherein the gradient map is configured to depict a plurality of temperatures of the tissue at the target site, at a selected depth below the surface of the patient's skin.

6. The system of claim 1, wherein the thermal transmitter includes a radiofrequency transmitter.

7. The system of claim 1, wherein the thermal transmitter includes a microwave transmitter.

8. The system of claim 1, wherein the member for immobilizing the body part is a frame.

9. The system of claim 1, wherein the member for immobilizing the body part is a clamp.

10. The system of claim 1, wherein the member for immobilizing the body part is a binding.

11. The system of claim 1, wherein the elapsed time is between about 0.1 minute and about 30 minutes.

12. The system of claim 11, wherein the elapsed time is between about 5 minutes and about 11 minutes.

13. The system of claim 12, wherein the wherein the elapsed time is about 7 minutes, and wherein the first temperature is between about 37 degrees Celsius and about 47 degrees Celsius.

14. The system of claim 12, wherein the elapsed time is about 10 minutes, and wherein the first temperature is between about. 37 degrees Celsius and about 47 degrees Celsius.

15. The system of claim 1, wherein the thermal imager comprises an imaging sensor operationally coupled to the processor, and wherein the imaging sensor includes a germanium lens.

16. The system of claim 1, wherein the thermal imager comprises a thermal camera.

17. The system of claim 1, wherein the thermal imager comprises a visible wavelength camera.

18. The system of claim 1, wherein the thermal transmitter includes an array of 2 to 200 radiofrequency or microwave emitters.

19. The system of claim 18, wherein the array is arranged in a grid.

20. The system of claim 18, wherein each of the radiofrequency or microwave emitters in the array is independently activated.

21. The system of claim 18, wherein at least two of the radiofrequency or microwave emitters in the array are independently movable.

22. The system of claim 21, wherein the at least two of the radiofrequency or microwave emitters in the array includes a first emitter and a second emitter, wherein the first emitter is configured to emit radiofrequency or microwave energy at the target site from a first angle, and wherein the second emitter is configured to emit radiofrequency or microwave energy at the target site from a second angle.

23. A radiofrequency or microwave energy treatment system, comprising:
a pod configured for housing a body part of a patient;
a member for immobilizing the body part selected from the group consisting of a frame, a clamp, and a binding;
an array of transmitters arranged on the inside surface of the pod, wherein each of the transmitters is a radiofrequency transmitter or a microwave transmitter;
a processor operationally coupled both to the array of transmitters and to a memory configured to store executable programs;
a controller operationally coupled to the processor and the memory, the controller configured to control operations of the array of transmitters, each transmitter in the array comprises an autonomous motorized mount operationally coupled to the controller, the autonomous motorized mount attaches its respective transmitter to the inside surface of the pod, and each of the transmitters in the array is configured to apply radiofrequency energy or microwave energy to a target site located on the patient's body part below the surface of the patient's skin to heat the target site to a temperature between about 35 degrees Celsius and about 50 degrees Celsius without burning the surface of the patient's skin; and
a thermal imager on the inside surface of the pod and operationally connected to the processor, wherein the thermal imager is configured to capture thermal data and thermal images of both the target site and the tissue surrounding the target site, and wherein when a captured thermal image of the target site indicates a selected temperature has been reached, the processor, memory and controller are configured to autonomously adjust the a array of transmitters to maintain the selected temperature at the target site for a selected time.

24. The system of claim 23, wherein each of the transmitters in the array is independently activated.

25. The system of claim 23, wherein at least two of the transmitters in the array are independently movable.

26. The system of claim 25, wherein the at least two transmitters are configured to apply radiofrequency energy to the same target site.

27. The system of claim 23, wherein the member is a frame.

28. The system of claim 23, wherein the member is a clamp.

29. The system of claim 23, wherein the member is a binding.

30. The system of claim 23, wherein each of the transmitters is a radiofrequency transmitter.

31. The system of claim 23, wherein each of the transmitters is a microwave transmitter.

32. A radiofrequency or microwave energy treatment system, comprising:
a pod configured for housing a body part of a patient;
a member for immobilizing the body part selected from the group consisting of a frame, a clamp, and a binding;
an array of transmitters arranged on the inside surface of the pod, each of the transmitters in the array is a radiofrequency transmitter or a microwave transmitter, and the array including a first transmitter and a second transmitter;
a processor operationally coupled both to the array of transmitters and to a memory configured to store executable programs;
a controller operationally coupled to the processor and the memory, the controller configured to control operations of the array of transmitters, each transmitter in the array comprises an autonomous motorized mount operationally coupled to the controller, the autonomous motorized mount attaching each respective transmitter in the array to the inside surface of the pod and configured for independently moving each transmitter in the array; and
a thermal imager on the inside surface of the pod and operationally connected to the processor, the thermal imager configured to capture thermal data and thermal images of a first target site and a second target site;
wherein the first transmitter is configured to apply radiofrequency energy or microwave energy to the first target site located on the patient's body part below the surface of the patient's skin to heat the first target site without burning the surface of the patient's skin,
wherein the second transmitter is configured to apply radiofrequency energy or microwave energy to the second target site located on the patient's body part below the surface of the patient's skin to heat second the second target site without burning the surface of the patient's skin,
wherein when a captured thermal image of the first target site indicates a first temperature has been reached, the processor, memory and controller are configured to autonomously adjust the first transmitter to maintain the first temperature at the target site for a first elapsed time, and
wherein when a captured thermal image of the second target site indicates a second temperature has been reached, the processor, memory and controller are configured to autonomously adjust the second transmitter to maintain the second temperature at the second target site for a second elapsed time.

33. The system of claim 32, wherein the member is a frame.

34. The system of claim 32, wherein the member is a clamp.

35. The system of claim 32, wherein the member is a binding.

36. The system of claim 32, wherein each of the transmitters in the array is a radiofrequency transmitter.

37. The system of claim 32, wherein each of the transmitters in the array is a microwave transmitter.

* * * * *

UNITED STATES PATENT AND TRADEMARK OFFICE
CERTIFICATE OF CORRECTION

PATENT NO.       : 9,198,735 B2
APPLICATION NO.  : 14/510047
DATED            : December 1, 2015
INVENTOR(S)      : Farhan Taghizadeh It is certified that error appears in the above-identified patent and that said Letters Patent is hereby corrected as shown below:

In the Specification

In column 4 at line 37, After "depth" insert --.--.

In the Claims

In column 27 at line 62, In Claim 1, change "the the" to --the--.

In column 27 at line 62, In Claim 1, after "surrounding" insert --the--.

In column 29 at line 64, In Claim 23, before "array" delete "a".

In column 30 at line 48, In Claim 32, after "to heat" delete "second".

Signed and Sealed this
Twenty-sixth Day of July, 2016

Michelle K. Lee
*Director of the United States Patent and Trademark Office*